(12) United States Patent
Bandman et al.

(10) Patent No.: US 7,947,804 B1
(45) Date of Patent: May 24, 2011

(54) VESICLE TRAFFICKING PROTEINS

(75) Inventors: Olga Bandman, Mountain View, CA (US); Preeti Lal, Santa Clara, CA (US); Karl J. Guegler, Menlo Park, CA (US); Purvi Shah, Sunnyvale, CA (US); Neil C. Corley, Mountain View, CA (US)

(73) Assignee: Incyte Corporation, Wilmington, DE (US)

( * ) Notice: Subject to any disclaimer, the term of this patent is extended or adjusted under 35 U.S.C. 154(b) by 0 days.

(21) Appl. No.: 09/556,178

(22) Filed: Apr. 20, 2000

Related U.S. Application Data

(62) Division of application No. 09/368,408, filed on Aug. 4, 1999, now Pat. No. 6,071,703, which is a division of application No. 08/967,364, filed on Nov. 7, 1997, now Pat. No. 5,989,859.

(51) Int. Cl.
| | | |
|---|---|---|
| C07K 14/00 | (2006.01) | |
| C07K 17/00 | (2006.01) | |
| C07H 21/02 | (2006.01) | |
| C07H 21/04 | (2006.01) | |

(52) U.S. Cl. ...................................................... 530/350
(58) Field of Classification Search .................. 530/350
See application file for complete search history.

(56) References Cited

OTHER PUBLICATIONS

Pevsner, J. et al., EMBL Accession No. Q15715 "Vacuolar Protein Sorting Homolog h-VPS45", Nov. 1, 1996.*
Piper, R.C. et al., "Yeast Vps45 is a Sec1p-like protein required for the consumption of vacuole targeted, post-Golgi transport vesicles", Europ. J. Cell Biology, vol. 65, pp. 305-318 (1994).*
Pevsner, J., "The Role of Sec1p-Related Proteins in Vesicle Trafficking in the Nerve Terminal", J. Neurosci. Res., vol. 45, pp. 89-95 (1996).*
Tellam, J.T. et al., "Identification of a Mammalian Golgi Sec1p-like Protein, mVps45", J. Biol. Chem., vol. 272, pp. 6187-6193.*
El Husseini, A. E-D. et al., "Molecular cloning of a mammalian homologue of the yeast vesicular transport protein vps45", BB Acta, vol. 1325, pp. 8-12 (1997).*
Rajasekariah, P. et al., "Molecular cloning and characterization of a cDNA encoding the human leucocyte vacuolar protein sorting (h1Vps45)", Int. J. Biochem. Cell Biol., vol. 31, pp. 683-694 (1999).*
Aalto, M., et al., "A Family of Proteins Involved in Intracellular Transport," Cell, 68:181-182 (1992).

El-Husseini, A., et al., Molecular cloning of a mammalian homologue of the yeast vesicular transport protein vps45, Biochimica et Biophysica Acta 1325:8-12 (1997).
Pevsner, J., et al., "Mammalian homologues of yeast vacuolar protein sorting (vps) genes implicated in Golgi-to-lysosome trafficking," Gene, 183:7-14.
Niu, S., et al., Cloning and sequencing of a developmentally regulated avian mRNA containing the LEA motif found in plant seed proteins, Gene, 175:187-191 (1996).
Kuge, O., et al., "ζ-COP, a Subunit of Coatomer, Is Required for COP-coated Vesicle Assembly," The Journal of Cell Biology, 123(6):1727-1734 (1993).
Tellam, J.T., et al., (GI 1703494), GenBank Sequence Database (Accession U66865), National Center for Biotechnology Information, National Library of Medicine, Bethesda, Maryland, 20894 (1996).
Tellam, J.T., et al., (GI 1703493), GenBank Sequence Database (Accession U66865), National Center for Biotechnology Information, National Library of Medicine, Bethesda, Maryland, 20894 (1996).
Niu, S., et al., (GI 969170),GenBank Sequence Database (Accession U31977), National Center for Biotechnology Information, National Library of Medicine, Bethesda, Maryland, 20894 (1996).
Niu, S., et al., (GI 969169),GenBank Sequence Database (Accession U31977), National Center for Biotechnology Information, National Library of Medicine, Bethesda, Maryland, 20894 (1996).
Kuge. O.,(GI 441486),GenBank Sequence Database (Accession X75935, National Center for Biotechnology Information, National Library of Medicine, Bethesda, Maryland, 20894 (1993).
Kuge. O.,(GI 441485),GenBank Sequence Database (Accession X75935, National Center for Biotechnology Information, National Library of Medicine, Bethesda, Maryland, 20894 (1993).
Adams, M.D. et al., Nature 377 (6547 Suppl.) 3-174 (1995).
Iadonato, S.P. et al., (g1808698) Accession No. AC000109, Sep. 11, 1997.
Iadonato, S.P. et al., (g1808699) Accession No. AC000110, Jan. 30, 1997.
GenBank Accession AA442417, "zv70e05.r1 Soares_total_fetus_Nb2HF8_9w Homo sapiens cDNA clone", submitted by Hillier et al., Jun. 2, 1997.
GenBank Accession U35246, "Human vacuolar protein sorting homolog h-vps45 mRNA, complete cds.", submitted by Pevsner et al., Jan. 15, 1997.

* cited by examiner

Primary Examiner — Teresa E Strzelecka
(74) Attorney, Agent, or Firm — Foley & Lardner LLP

(57) ABSTRACT

The invention provides three human vesicle trafficking proteins (VTP) and polynucleotides which identify and encode VTP. The invention also provides expression vectors, host cells, agonists, antibodies and antagonists. The invention also provides methods for preventing and treating disorders associated with expression of VTP.

6 Claims, 26 Drawing Sheets

```
                                                                         54
5' NGG ACC TCG CGT CGG GAA AGA CTG CGG GGT TAA TTT AGC CAG ACA CGT GGG

108
CGG GAA GGG CTG TAG GGT ACT TGT CAA TTC GCC ATG AAC GTG GTT TTT GCT
                                                                M   N   V   V   F   A 117                 126         135         144         153         162
GTG AAG CAG TAC ATT TCC AAA ATG ATA GAG GAC AGC GGG CCT GGT ATG AAA GTA
 V   K   Q   Y   I   S   K   M   I   E   D   S   G   P   G   M   K   V 171                 180         189         198         207         216
CTT CTC ATG GAT AAA GAG ACG ACT TGT CAA TTC GGC ATA GTG AGT ATG TAC ACA CAA TCG
 L   L   M   D   K   E   T   T           G   I   V   S   M   Y   T   Q   S 225                 234         243         252         261         270
GAG ATT CTA CAG AAG GAA GTG TAC CTC TTT GAA CGC ATC GAT TCT CAA AAT CGA
 E   I   L   Q   K   E   V   Y   L   F   E   R   I   D   S   Q   N   R 279                 288         297         306         315         324
GAG ATC ATG AAA CAC CTG AAG GCA ATT TGT TTT CTT CGA CCT ACA AAG GAG AAT
 E   I   M   K   H   L   K   A   I   C   F   L   R   P   T   K   E   N 333                 342         351         360         369         378
GTG GAT TAT ATT ATT CAG GAG CTC CGA AGA CCC AAA TAC ACT ATA TAT TTC ATT
 V   D   Y   I   I   Q   E   L   R   R   P   K   Y   T   I   Y   F   I

FIGURE 1A
```

```
     387           396           405           414           423           432
TAT TTC AGT AAT GTG ATC AGC AAG AGT GAC GTG AAG TCA TTG GCT GAA GCT GAT
 Y   F   S   N   V   I   S   K   S   D   V   K   S   L   A   E   A   D 441           450           459           468           477           486
GAA CAG GAA GTT GTG GCT GAG GTT CAG GAA TTT TAT GGT GAT TAC ATT GCT GTG
 E   Q   E   V   V   A   E   V   Q   E   F   Y   G   D   Y   I   A   V 495           504           513           522           531           540
AAC CCA CAT TTG TCC CTC AAT ATT TTG GGT TGC CAG GGT CGA AAT TGG
 N   P   H   L   F   S   L   N   I   L   G   C   Q   G   R   N   W 549           558           567           576           585           594
GAT GCC CAG CTA TCT AGA ACA ACT CAA GGG CTT ACA GCT CTC CTT TTA TCT
 D   A   Q   L   S   R   T   T   Q   G   L   T   A   L   L   L   S 603           612           621           630           639           648
CTG AAG TGT CCC ATG ATT CGT TAT CAG CTC TCA GAG TCA GCA AAG AGA
 L   K   C   P   M   I   R   Y   Q   L   S   E   S   A   K   R 657           666           675           684           693           702
CTT GCA GAG TGC GTT AAG CAA GTG ATA ACT AAA GAA TAT GAA CTG TTT GAA TTC
 L   A   E   C   V   K   Q   V   I   T   K   E   Y   E   L   F   E   F 711           720           729           738           747           756
CGT CGG ACA GAG GTT CCT CCA TTG CTC CTT ATT TTA GAT CGC TGT GAT GAT GCC
 R   R   T   E   V   P   P   L   L   L   I   L   D   R   C   D   D   A
```

FIGURE 1B

```
       765        774        783        792        801        810
ATC ACC CCA TTG CTA AAC CAG TGG ACA TAT CAG GCC ATG GTC CAC GAA CTA CTA
 I   T   P   L   L   N   Q   W   T   Y   Q   A   M   V   H   E   L   L 819        828        837        846        855        864
GGC ATA AAC AAC AAT CGG ATT GAT CTT TCC AGA GTG CCG GGA ATC AGT AAA GAC
 G   I   N   N   N   R   I   D   L   S   R   V   P   G   I   S   K   D 873        882        891        900        909        918
TTA AGA GAA GTG GTC CTA TCT GCT GAA AAT GAT GAA TTC TAT GCT AAT AAT ATG
 L   R   E   V   V   L   S   A   E   N   D   E   F   Y   A   N   N   M 927        936        945        954        963        972
TAC CTG AAC TTT GCT GAG ATT GGT AGC AAT ATA AAG AAT CTC ATG GAA GAT TTT
 Y   L   N   F   A   E   I   G   S   N   I   K   N   L   M   E   D   F 981        990        999       1008       1017       1026
CAG AAG AAA CCA AAA GAA CAG CAA AAA CTA GAA TCA ATA GCA GAC ATG AAG
 Q   K   K   P   K   E   Q   Q   K   L   E   S   I   A   D   M   K 1035       1044       1053       1062       1071       1080
GCG TTT GTT GAG AAT TAT CCA CAG TTC AAG AAA ATG TCT GGG ACT GTT TCA AAG
 A   F   V   E   N   Y   P   Q   F   K   K   M   S   G   T   V   S   K 1089       1098       1107       1116       1125       1134
CAT GTG ACA GTG GTT GGA GAA CTG TCT CGA TTG GTC AGT GAA CGG AAT CTG CTG
 H   V   T   V   V   G   E   L   S   R   L   V   S   E   R   N   L   L

FIGURE 1C
```

```
      1143             1152             1161             1170             1179             1188
GAG GTT TCA GAG GTT GAG CAA GAA CTG GCC TGT CAA AAT GAC CAT TCT AGT GCT
 E   V   S   E   V   E   Q   E   L   A   C   Q   N   D   H   S   S   A 1197             1206             1215             1224             1233             1242
CTC CAG AAT ATA AAA AGG CTT CTG CAG AAC CCC AAA GTG ACA GAG TTT GAT GCT
 L   Q   N   I   K   R   L   L   Q   N   P   K   V   T   E   F   D   A 1251             1260             1269             1278             1287             1296
GCC CGC CTG ATG CTG GTG CTT TAT GCT CTT CAT TAT GAG CGA CAC AGC AAT AGC
 A   R   L   M   L   V   L   Y   A   L   H   Y   E   R   H   S   N   S 1305             1314             1323             1332             1341             1350
CTG CCA GGA CTA ATG GAC ATG GAC CTC AGG AAT AAA GGT GTT TCT GAG AAG TAT CGA
 L   P   G   L   M   D   M   D   L   R   N   K   G   V   S   E   K   Y   R 1359             1368             1377             1386             1395             1404
AAG CTC GTG TCT GCA GTT GTT GAA TAT GGT GGT AAA CGA GTC AGA GGA AGT GAC
 K   L   V   S   A   V   V   E   Y   G   G   K   R   V   R   G   S   D 1413             1422             1431             1440             1449             1458
CTC TTC AGC CCC AAA GAT GCT GTG GCT ATC ACC AAA CAA TTC CTC AAA GGA CTG
 L   F   S   P   K   D   A   V   A   I   T   K   Q   F   L   K   G   L 1467             1476             1485             1494             1503             1512
AAG GGA GTA GAA AAT GTA TAT ACA CAG CAT CAA CCT TTC CTA CAT GAA ACC CTG
 K   G   V   E   N   V   Y   T   Q   H   Q   P   F   L   H   E   T   L
```

FIGURE 1D

```
        1521          1530          1539          1548          1557          1566
GAT CAT CTC ATC AAA GGA AGG CTT AAG GAA AAC CTA TAT CCT TAT TTA GGC CCC
 D   H   L   I   K   G   R   L   K   E   N   L   Y   P   Y   L   G   P 1575          1584          1593          1602          1611          1620
AGC ACA CTC AGA GAC AGA CCT CAG GAT ATC ATT GTG TTT GTA ATT GGA GGA GCC
 S   T   L   R   D   R   P   Q   D   I   I   V   F   V   I   G   G   A 1629          1638          1647          1656          1665          1674
ACC TAT GAA GAG GCT CTA ACA GTT TAT AAC CTG AAC CGC ACC ACT CCT GGA GTG
 T   Y   E   E   A   L   T   V   Y   N   L   N   R   T   T   P   G   V 1683          1692          1701          1710          1719          1728
AGG ATT GTC CTG GGA GGC ACC ACA GTG CAC AAC ACG AAA AGT TTC CTA GAG GAA
 R   I   V   L   G   G   T   T   V   H   N   T   K   S   F   L   E   E 1737          1746          1755          1764          1773          1782
GTT CTG GCT TCT GGA CTG CAC AGC CGA AGC AAG GAG AGC TCT CAA GTC ACA TCA
 V   L   A   S   G   L   H   S   R   S   K   E   S   S   Q   V   T   S 1791          1800          1809          1818          1827          1836
AGG TCA GCG AGC AGA AGA TGA AAC GGT GGT TGG GGG AAG GGC ACA GCT TCC TCT
 R   S   A   S   R   R   *

1845          1854          1863          1872          1881          1890
CTT GTC CCC ACT ACA GGT TTT CCC TAC TAA ACA AAG GTG TTG GAG AGC AGC TTT
```

FIGURE 1E

```
      1899        1908        1917        1926        1935        1944
GGG TTC TGT GCT GGT TGT TAG AAC TCA TCT CCA GGT AGC CCA CGG ATA CGT GGT 1953        1962        1971        1980        1989        1998
TGG CAC AGA CAC AAG ACT CCC AGA GTT GTC CTA ACA ATA AGT CTG AGC CCA TCT 2007        2016        2025        2034        2043        2052
CAA CCC ACT TTT CTC CGG TAG TCT TTA TGT ATC TGT TAG CAC AAT CAC TTC AGT 2061        2070        2079        2088        2097        2106
TAC TGA TGA ATT TTG GGA TCT GAC TTG GGG AAA GGG TTA TCA GAG CCT AGA 2115        2124        2133        2142        2151        2160
GGG GCT TAA AAA GTA ATC ATT TGA TGT ACA TAC CAC ACT CCT TGG CTT CCT TTC 2169        2178        2187        2196        2205        2214
TCT TCC CTT AAC CCT TTC TGC TTT TCA TTA ACC ACA TTC CTG CAC AAC TCA TTT 2223        2232        2241        2250        2259        2268
CTG AAA ACC TAC CAT GTT TCT TTA CAG AGC CAT CCA AAA ATT TTT TGT CCC TAC
```

FIGURE 1F

```
     2277      2286      2295      2304      2313      2322
ATA GCA ATT TTC TGT GGC ACT GAG AAA CCA TGT ATG ACC ACA ATA AAA ATC CAT 2331      2340
TTT GTG AAA GGA AAA AAA AAA  3'
```

```
                         9              18             27             36             45             54
5' NGA GCG GGG     CAG GTG TAG     CCT CTG TGC     CTC GTT GTC     CCC TGG CGC     TAC 63              72             81             90             99            108
   CCG GAC ATC     TCT CAG GGT     GCC GGC ACC     ATG AAG ATC     TGG ACT TCG     GAG CAC GTC
                                                    M   K   I       W   T   S       E   H   V 117             126            135            144            153            162
   TTT GAC CAC     CCG TGG GAA     ACT GTT ACA     ACA GCT GCA     ATG CAG AAA     TAC CCA AAC
    F   D   H       P   W   E       T   V   T       T   A   A       M   Q   K       Y   P   N 171             180            189            198            207            216
   CCT ATG AAC     CCA AGT GTG     GTT GGA GAT     GTG TTG GAC     AGA CAT ATA     GAT CCC
    P   M   N       P   S   V       V   G   D       V   L   D       R   H   I       D   P 225             234            243            252            261            270
   TCT GGA AAG     TTG CAC AGC     CAC AGA CTT     CTC AGC ACA     GAG TGG GGA     CTG CCT TCC
    S   G   K       L   H   S       H   R   L       L   S   T       E   W   G       L   P   S 279             288            297            306            315            324
   ATT GTG TCT     CTT ATT GGT     GCA GCA ACG     AGA ACA TAT     GTG CAA GAA     CAT
    I   V   S       L   I   G       A   A   T       R   T   Y       V   Q   E       H 333             342            351            360            369            378
   TCT GTA GTT     GAT CCT GTA     GAC AAA ACA     ATG GAA CTT     AAA TCT ACT     AAT ATT TCA
    S   V   V       D   P   V       E   K   T       M   E   L       K   S   T       N   I   S
```

FIGURE 4A

```
           387        396        405        414        423        432
TTT ACA AAC ATG GTT TCA GTA GAT GAG AGA CTT ATA TAC AAA CCA CAT CCT CAG
 F   T   N   M   V   S   V   D   E   R   L   I   Y   K   P   H   P   Q 441        450        459        468        477        486
GAT CCA GAA AAA ACT GTT TTG ACA CAA GAA GCC ATA ATT ACC GTG AAA GGA GTT
 D   P   E   K   T   V   L   T   Q   E   A   I   I   T   V   K   G   V 495        504        513        522        531        540
AGC CTC AGC AGT TAC CTT GAA GGA ATG GCA CTG ATA AGT ACG TCC TCA AAT GCT
 S   L   S   S   Y   L   E   G   M   A   L   I   S   T   S   S   N   A 549        558        567        576        585        594
AGT AAA GGC CGA GAA ATG GCA TGG GTA ATA CAT AAA TTA AAT GCT GAG ATT
 S   K   G   R   E   M   A   W   V   I   H   K   L   N   A   E   I 603        612        621        630        639        648
GAA CTG ACA GCC TCA GCA AGA GGA ACC ATA AGG ACT CCA ATG GCA GCA GCA
 E   L   T   A   S   A   R   G   T   I   R   T   P   M   A   A   A 657        666        675        684        693        702
GAA GAA GCA GAG AAG TGA TCG TGA TCG TGA CAG TTG GTA GAC AAC ATC GGG TAC TCC AGG
 E   E   A   E   K 711        720        729        738        747        756
GCG TTT CAA ACT GAC TAT ATA TTT ATT TGT TAT TTT AAA AAT ACA ACT ATA TTT
 A   F
TCT CTC CAA ACT GAC TAT ATA TTT ATT TGT TAT TTT AAA AAT ACA ACT ATA TTT
```

FIGURE 4B

```
      765         774        783                    792            801           810
TGG GTA GTT TTT TTT TTT TTT GAT AAG TTG GTG TAA GGC TAT GTG ACT 819             828        837
GAT CAA AAC AGA TGC AGG GCC TCT AAA 3'
```

FIGURE 4C

```
1    MKIWTSEHVFDHPWETVTTAAMQKYPNPMNPSVVGVDVLD    2056691
1    MGKYCASLGVLKGPWDQVFAAFWQRYPNPYSKHVLTEDIV    GI 969170

41   RHIDPSGKLHSHRLLSTEWGLPSIVKSLIGAARTKTYVQE    2056691
41   HREVTADHKLLSRLLTKTNRMPRWAERFFPANVAHNVYI     GI 969170

81   HSVVDPVEKTMELKSTNISFTNMVSVDERLIYKPHPQDPE    2056691
81   VEDSIVDPKNRTMTTFTWNINHARLMAVEERCVYRVNPEN    GI 969170

121  KTVLTQEAIITVKGVSLSSYLEGLMASTISSNASKGREAM    2056691
121  SSWTEVKREAWVSSSLFGVSRAVQEFGLARFKSNVTKSTK    GI 969170

161  EWVIHKLNAEIEELTASARGTIRTPMAAAAFAEK          2056691
161  GFEYVLARMQGEAPSKTLVETAKEATEKAKETALAATEKA    GI 969170

194                                             2056691
201  KDLASKAATKKQFV                             GI 969170
```

FIGURE 5

```
                  9                  18                 27                 36                 45                 54
5' NGG CCA ATC AGC GGC GTT TCT TTT GCG GCT CCA CGT CGG CAC CAG CTG CGG 63                 72                 81                 90                 99                108
GGC AAG ATG GAG GCG CTG ATT TTG GAA CCT TCC CTG TAT ACT GTC AAA GCC ATC
        M   E   A   L   I   L   E   P   S   L   Y   T   V   K   A   I 117                126                135                144                153                162
CTG ATT CTG GAC AAT GAT GGA GAT CGA CTT TTT GCC AAG TAC TAT GAC GAC ACC
 L   I   L   D   N   D   G   D   R   L   F   A   K   Y   Y   D   D   T 171                180                189                198                207                216
TAC CCC AGT GTC AAG CAA AAG GAG GCC TTT GAG AAG AAC ATT TTC AAC AAG ACC
 Y   P   S   V   K   Q   K   E   A   F   E   K   N   I   F   N   K   T 225                234                243                252                261                270
CAT CGG ACT GAC AGT GAA ATT GCC CTC TTG GAA GGC CTG ACA GTG GTA TAC AAA
 H   R   T   D   S   E   I   A   L   L   E   G   L   T   V   V   Y   K 279                288                297                306                315                324
AGC AGT ATA GAT CTC TAT TTC TAT GTG ATT GGC AGC TCC TAT GAA AAT GAG CTG
 S   S   I   D   L   Y   F   Y   V   I   G   S   S   Y   E   N   E   L 333                342                351                360                369                378
ATG CTT ATG GCT GTT CTG AAC TGT CTC TTC GAC TCA TTG AGC CAG ATG CTG AGG
 M   L   M   A   V   L   N   C   L   F   D   S   L   S   Q   M   L   R
```

FIGURE 7A

```
       387            396            405            414            423            432
AAA AAT GTA GAA AAG CGA GCA CTG GAG AAC ATG GAG GGG CTG TTC TTG GCT
 K   N   V   E   K   R   A   L   E   N   M   E   G   L   F   L   A 441            450            459            468            477            486
GTG GAT GAA ATT GTA GAT GGA GGG GTG ATC CTA GAG AGT GAT CCC CAG CAG GTG
 V   D   E   I   V   D   G   G   V   I   L   E   S   D   P   Q   Q   V 495            504            513            522            531            540
GTA CAC CGG GTG GCA TTA AGG GGT GAA GAT GTC CCC CTT ACG GAG CAG ACC GTG
 V   H   R   V   A   L   R   G   E   D   V   P   L   T   E   Q   T   V 549            558            567            576            585            594
TCT CAG GTG CTG CAG TCA GCC AAA GAA CAG ATC AAG TGG TCA CTC CTT CGG TGA
 S   Q   V   L   Q   S   A   K   E   Q   I   K   W   S   L   L   R 603            612            621            630            639            648
AGA CCT CAC TGT TCC TGG CTC ATC CTC TTC AAA TTT GCA TGT CTG CTG 657            666            675            684            693            702
TGA ATT TTC ATC TAG TTC CCC AAT CGA TGC TCT CAG GGT CAT CTC GGG GAT CAC 711            720            729            738            747            756
AGG GAT CCT TAA ATC TCC ATT CTG TTT GTG GTT GCC CCC TCA ACC TCC CCT ACA
```

FIGURE 7B

```
       765        774        783        792       801        810
CCC TTC CTA TTC TTT ATT CTT GCA GTT CTG GGA GTA AAG CTC CCA GCA 819        828        837        846       855        864
TAT TTA GAT AAT AGG GCA GGG GAA GCA CCC TCT TTC TTT CTA GAC TGG ATT ATG 873        882        891        900       909        918
CTC ACA TGC TCC CTT GCC CTG ACA TTT TTG TAA ATT CTG TGC CCT TTG CTG TAG 927        936        945        954       963        972
CTA CAC TTC AGA TTA AAG TAG GAG AAA GAA TGT GCT GAG TGT TTT CCT CCC TTT 981        990        999       1008      1017       1026
GCC TCT ACC TGG CCC TCA TCC CAA CAG CCC AGC AAG GGG AGA GAG AAA GAG AAT 1035       1044       1053       1062      1071       1080
TCT TTT CTA TAG AAC GAG TGG GGG CGG GGA TGG GTA GGG ATT TAT CCA ATC TAA 1089       1098       1107       1116      1125       1134
GCC CTA ACC CCA CTT AGT GAC CTC AGT GTT TTC CAT TCC TTC TTA CTG CCC
```

FIGURE 7C

```
      1143           1152           1161           1170           1179           1188
TGT CCT CTG    CCT TGG AAG    AGG CTT TGG    GAA TAG TTC    ATA GGG AAG    GGA CAA CAT 1197           1206           1215           1224           1233           1242
GGA AGA AAC    AGC GAT TTA    AAT TGT ATT    GAA CAG GGC    ATA TAA AAT    GCA TTC TGT 1251           1260           1269           1278           1287           1296
ACC CTG ATC    TGG CAT ATA    GCT TCA AAA    CTG CAG TGG    CGA GTG TCC    ATC TCT TAG 1305           1314           1323           1332           1341           1350
TTA GCT ACC    TTA ACT GTC    CAC CCT TAC    TAC CTG TGG    GAT CGT TGC    CTG GTT TGT 1359           1368           1377           1386           1395           1404
CTT CTC TGT    GTC CTG GAG    CAA AGC CAG    TTC CTA AAA    CTA AAA CTC    CAT TCT AGT
 L   L   C      V   L   E      Q   S   Q      F   L   K      L   K   L      H   S   S 1413           1422           1431           1440           1449           1458
CTT GGG AAG    AAA AGT TTC    TAC TCA GAA    CTG GGG AAG    GAG TGG AAC    TTA TGA CTT 1467           1476           1485           1494           1503           1512
GGG CCT CTA    GGC TGT CTC    TGT CCC CTC    AGC TCC CCG    ACA TGC ATT    TAC TCT CTG
```

FIGURE 7D

```
       1521        1530        1539        1548        1557        1566
CCG TGG GTC TGC AGT CGC TGC AAC CTA CCC TCT CTC TGC CTC AGC CTT ACA CCC 1575        1584        1593        1602        1611        1620
AAG CAG TAG GTC TGT GCT CTC CCT GTC TCT AGG TCG CTG AGA GAG GTG CTT TTC 1629        1638        1647        1656        1665        1674
TTC ATA AAA CCT TTG GGG TTT CCC CAG GAA GAT GGA GAA TGG AAT ACT 1683        1692        1701        1710        1719        1728
CAC TCT TGG GTC TAA TCT TTC CCC TTG ACC CAG AAC TTC CTC CCC ACA AAA ATG 1737        1746        1755        1764        1773        1782
CCT TTA AAA ACC TTC CTG AGA CTT AAG CAT TCT GCC CCA CTT ACT AAC TGC CAG 1791        1800        1809        1818        1827        1836
TTC TCC AGC ACT GAG GTG GGG CAG ATA ACT GGG CAT ATT TAA GGG GGC ATC TTT 1845        1854        1863        1872        1881        1890
GTG TAA AAG ATG CAT GGA GTC AGG AGA AAA CCA CCT TCA TAA ACT GCT CTG TGC
```

FIGURE 7E

```
     1899        1908        1917       1926
AAA GAG GAA TAA AAC ATT TTT TCC AAA AAA AAA AAA AAA AAA A 3
```

VESICLE TRAFFICKING PROTEINS

This application is a divisional application of U.S. application Ser. No. 09/368,408, filed Aug. 4, 1999, now U.S. Pat. No. 6,071,703 which is a divisional application of U.S. application Ser. No. 08/967,364, filed on Nov. 7, 1997, now U.S. Pat. No. 5,989,859, issued Nov. 23, 1999, both entitled VESICLE TRAFFICKING PROTEINS, all of which applications and patents are hereby incorporated herein by reference.

FIELD OF THE INVENTION

This invention relates to nucleic acid and amino acid sequences of three new human vesicle trafficking proteins and to the use of these sequences in the diagnosis, prevention, and treatment of inflammation and disorders associated with cell proliferation and apoptosis.

BACKGROUND OF THE INVENTION

Vesicle trafficking is defined as the vesicular transport of materials between different subcellular compartments of eukaryotic cells. Vesicles bud from a donor membrane and fuse with a recipient one carrying internalized materials from one site to another. Several protein complexes involving integral proteins of the vesicle and target membranes, such as Sec proteins and Rab proteins, help regulate vesicular transport by directing the vesicles to and from the correct membrane surface.

Sec1 is a member of a family of proteins which mediate vesicle trafficking. The Sec1 family consists of four members, Sec1, Vps33, Vps45, and Sly1. Specifically, Sec1 regulates transport from the endoplasmic reticulum (ER) to the Golgi complex; Vps33 participates in transport from a prevacuolar compartment to the vacuole; Vps45 is essential for transport from the Golgi to a prevacuolar compartment; and Sly1 is involved in transport from the ER to the Golgi. The yeast Sec1 proteins are hydrophilic, 80 kDa in size, and have about 20-24% sequence identity (Aalto, M. et al. (1992) Cell 68: 181-182). Rat Sec1, a mammalian homolog of the yeast Sec1, binds syntaxin, a plasma membrane protein localized in the active zone of axon terminals and essential for synapsis. Rat Vps33a and Vps33b and human Vps45, however, do not bind any of the known syntaxins. Northern analysis shows that rat Vps33, rat Vps45 and human Vps45 are expressed in brain, spleen, lung, liver, skeletal muscle, kidney, and testis. These results suggest that the mammalian proteins are essential in mediating transport among the Golgi complex, synaptic vesicles, prelysosomal compartments, and the lysosome (El-Husseini, A. E.-D. et al. (1997) Biochim. Biophys. Acta 1325: 8-12; and Pevsner, J. et al. (1996) Gene 183: 7-14).

Assembly protein complexes (APs) are essential for the assembly of clathrin-coated vesicles which participate in intracellular vesicle transport and receptor-mediated endocytosis. APs consist of two classes of homologous heterotetrameric complexes, AP-1 and AP-2, each of which is composed of two large chains, a medium chain, and a small chain. AP-1 functions in the Golgi complex, and AP-2 is localized in the plasma membrane and on the surface of endosomes. Avian px19 is an AP-small-chain homolog and possesses the LEA (late embryogenesis abundant) motif found in plant seed proteins. Developmental data suggest that px19 may be involved in hematopoiesis during avian development (Niu, S. et al. (1996) Gene 175: 187-191).

Non-clathrin-coated vesicles function in transporting proteins from the ER to the Golgi. These vesicles are coated with a family of AP-homologous proteins, the COP-proteins, which exist in the cytosol of eukaryotic cells as a complex, named coatomer. The ζ subunit of the COP coatomer is 20 kDa and has sequence similarity to the small chains of the AP complexes. Unlike other coatomer subunits, ζCOP is found in both coatomer-bound and coatomer-free cell extract fractions. Polyclonal antibody specific for ζCOP blocks the binding of the coatomer to the Golgi membrane, and thereby prevents the assembly of COP-coated vesicles on the Golgi cisternae (Kuge, O. et al. (1993) J. Cell Biol. 123: 1727-1734).

The discovery of three new human vesicle trafficking proteins and the polynucleotides encoding them satisfies a need in the art by providing new compositions which are useful in the diagnosis, prevention, and treatment of inflammation and disorders associated with cell proliferation and apoptosis.

SUMMARY OF THE INVENTION

The invention features a substantially purified human vesicle trafficking protein (VTP) comprising an amino acid sequence selected from the group consisting of SEQ ID NO:1, SEQ ID NO:3, and SEQ ID NO:5.

The invention also provides a variant of human vesicle trafficking protein having at least 90% amino acid identity to the amino acid sequence of VTP and which retains at least one functional characteristic of human VTP.

The invention further provides an isolated and substantially purified polynucleotide sequence encoding a VTP comprising the amino acid sequence of SEQ ID NO:1, SEQ ID NO:3, or SEQ ID NO:5, and a composition comprising the polynucleotide sequence, or a fragment thereof. The invention also provides a polynucleotide sequence which hybridizes to the polynucleotide sequence encoding VTP, or a fragment of the polynucleotide sequence. The invention further provides a polynucleotide sequence comprising the complement of the polynucleotide sequence encoding VTP or a fragment or variant of the polynucleotide sequence.

The invention further provides an isolated and purified polynucleotide sequence selected from the group consisting of SEQ ID NO:2, SEQ ID NO:4, and SEQ ID NO:6, or a fragment or a variant of the polynucleotide sequence. In addition, the invention provides a polynucleotide sequence which hybridizes to the polynucleotide sequence of SEQ ID NO:2, SEQ ID NO:4, or SEQ ID NO:6. The invention also provides a polynucleotide sequence which is complementary to SEQ ID NO:2, SEQ ID NO:4, or SEQ ID NO:6, or a fragment or a variant of the polynucleotide sequence The present invention further provides an expression vector containing at least a fragment of a polynucleotide sequence which encodes VTP comprising the amino acid sequence of SEQ ID NO:1, SEQ ID NO:3, or SEQ ID NO:5. In yet another aspect, the expression vector containing the polynucleotide sequence is contained within a host cell.

The invention also provides a method for producing VTP, or a fragment of VTP, the method comprising the steps of: a) culturing a host cell containing an expression vector containing at least a fragment of a polynucleotide sequence encoding VTP under conditions suitable for the expression of the polypeptide; and b) recovering the polypeptide from the host cell culture.

The invention also provides a pharmaceutical composition comprising a substantially purified VTP having the amino acid sequence of SEQ ID NO:1, SEQ ID NO:3, or SEQ ID NO:5, in conjunction with a suitable pharmaceutical carrier.

The invention also provides a purified antagonist of VTP. In one aspect, the invention provides a purified antibody which binds to VTP.

Still further, the invention provides a purified agonist of VTP.

The invention also provides a method for stimulating cell proliferation comprising administering to a cell an effective amount of purified VTP.

The invention also provides a method for preventing or treating a disorder associated with an increase in apoptosis comprising administering to a subject in need of such treatment an effective amount of a pharmaceutical composition comprising purified VTP.

The invention also provides a method for preventing or treating a cancer comprising administering to a subject in need of such treatment an effective amount of an antagonist of VTP.

The invention also provides a method for preventing or treating an inflammation comprising administering to a subject in need of such treatment an effective amount of an antagonist of VTP.

The invention also provides a method for detecting a polynucleotide which encodes VTP in a biological sample comprising the steps of: a) hybridizing the complement of the polynucleotide sequence which encodes VTP to nucleic acid material of a biological sample, thereby forming a hybridization complex; and b) detecting the hybridization complex, wherein the presence of the complex correlates with the presence of a polynucleotide encoding VTP in the biological sample. In one aspect, the nucleic acid material of the biological sample is amplified by the polymerase chain reaction prior to hybridization.

BRIEF DESCRIPTION OF THE FIGURES

FIGS. 1A, 1B, 1C, 1D, 1E, 1F, and 1G show the amino acid sequence (SEQ ID NO:1) and nucleic acid sequence (SEQ ID NO:2) of VTP-1. The alignment was produced using MACDNASIS PRO software (Hitachi Software Engineering Co. Ltd. San Bruno, Calif.).

FIGS. 2A and 2B show the amino acid sequence alignments between VTP-1 (75871; SEQ ID NO:1), a mouse vacuolar protein-sorting protein, mVps45 (GI 1703494; SEQ ID NO:7), produced using the multisequence alignment program of DNASTAR software (DNASTAR Inc., Madison, Wis.).

FIGS. 4A, 4B, and 4C show the amino acid sequence (SEQ ID NO:3) and nucleic acid sequence (SEQ ID NO:4) of VTP-2. The alignment was produced using MACDNASIS PRO software (Hitachi Software Engineering Co. Ltd. San Bruno, Calif.).

FIG. 5 shows the amino acid sequence alignments between VTP-2 (2056691; SEQ ID NO:3) and an avian homolog of AP small chains, px19 (GI 969170; SEQ ID NO:8), produced using the multisequence alignment program of DNASTAR software (DNASTAR Inc., Madison Wis.).

FIGS. 7A, 7B, 7C, 7D, 7E, and 7F show the amino acid sequence (SEQ ID NO:5) and nucleic acid sequence (SEQ ID NO:6) of VTP-3. The alignment was produced using MACDNASIS PRO software (Hitachi Software Engineering Co. Ltd. San Bruno, Calif.).

FIG. 8 shows the amino acid sequence alignments between VTP-3 (3086794; SEQ ID NO:5) and a subunit of a cow coatomer, ζCOP (GI 441-486; SEQ ID NO:9), produced using the multisequence alignment program of DNASTAR software (DNASTAR Inc., Madison, Wis.).

DESCRIPTION OF THE INVENTION

Figure 3A:
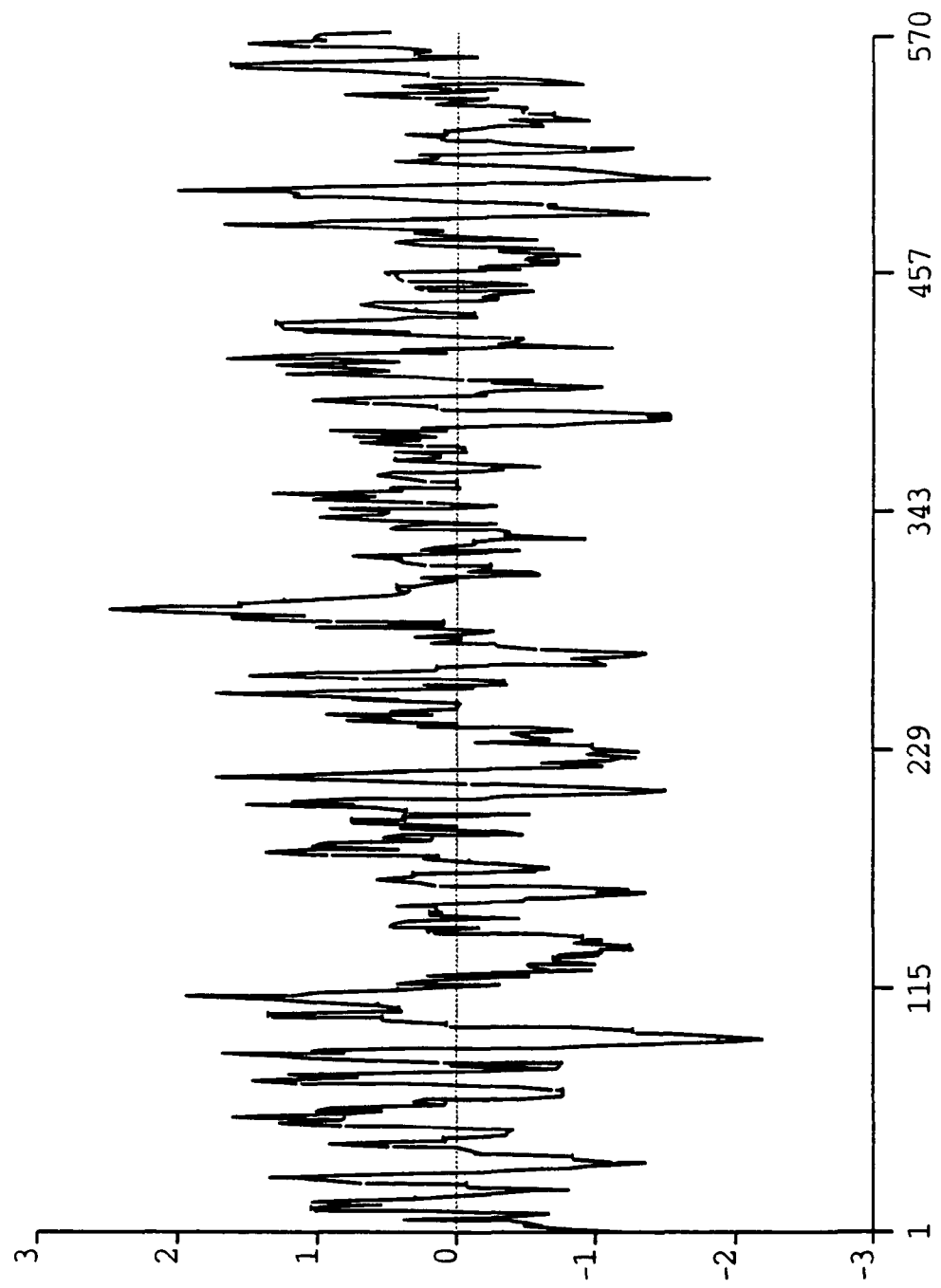
FIGS. 3A and 3B show the hydrophobicity plots for VTP-1 (SEQ ID NO:1) and mVps45 (SEQ ID NO:7), respectively. The positive X axis reflects amino acid position, and the negative Y axis, hydrophobicity (MACDNASIS PRO software).

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise.

Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

DEFINITIONS

VTP, as used herein, refers to the amino acid sequences of substantially purified VTP obtained from any species, particularly mammalian, including bovine, ovine, porcine, murine, equine, and preferably human, from any source whether natural, synthetic, semi-synthetic, or recombinant.

The term "agonist", as used herein, refers to a molecule which, when bound to VTP, increases or prolongs the duration of the effect of VTP. Agonists may include proteins, nucleic acids, carbohydrates, or any other molecules which bind to and modulate the effect of VTP.

An "allele" or "allelic sequence", as used herein, is an alternative form of the gene encoding VTP. Alleles may result from at least one mutation in the nucleic acid sequence and may result in altered mRNAs or polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

"Altered" nucleic acid sequences encoding VTP as used herein include those with deletions, insertions, or substitutions of different nucleotides resulting in a polynucleotide that encodes the same or a functionally equivalent VTP. Included within this definition are polymorphisms which may or may not be readily detectable using a particular oligonucleotide probe of the polynucleotide encoding VTP, and improper or unexpected hybridization to alleles, with a locus other than the normal chromosomal locus for the polynucleotide sequence encoding VTP. The encoded protein may also be "altered" and contain deletions, insertions, or substitutions of amino acid residues which produce a silent change and result in a functionally equivalent VTP. Deliberate amino acid substitutions may be made on the basis of similarity in polarity, charge, solubility, hydrophobicity, hydrophilicity, and/or the amphipathic nature of the residues as long as the biological or immunological activity of VTP is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine, glycine and alanine, asparagine and glutamine, serine and threonine, and phenylalanine and tyrosine.

"Amino acid sequence" as used herein refers to an oligopeptide, peptide, polypeptide, or protein sequence, and fragment thereof, and to naturally occurring or synthetic molecules. Fragments of VTP are preferably about 5 to about 15 amino acids in length and retain the biological activity or the immunological activity of VTP. Where "amino acid sequence" is recited herein to refer to an amino acid sequence of a naturally occurring protein molecule, amino acid sequence, and like terms, are not meant to limit the amino acid sequence to the complete, native amino acid sequence associated with the recited protein molecule.

"Amplification" as used herein refers to the production of additional copies of a nucleic acid sequence and is generally carried out using polymerase chain reaction (PCR) technologies well known in the art (Dieffenbach, C. W. and G. S. Dveksler (1995) *PCR Primer, a Laboratory Manual*, Cold Spring Harbor Press, Plainview, N.Y.).

The term "antagonist" as used herein, refers to a molecule which, when bound to VTP, decreases the amount or the duration of the effect of the biological or immunological activity of VTP. Antagonists may include proteins, nucleic acids, carbohydrates, antibodies or any other molecules which decrease the effect of VTP.

As used herein, the term "antibody" refers to intact molecules as well as fragments thereof, such as Fab, F(ab')$_2$, and Fv, which are capable of binding the epitopic determinant. Antibodies that bind VTP polypeptides can be prepared using intact polypeptides or fragments containing small peptides of interest as the immunizing antigen. The polypeptide or oligopeptide used to immunize an animal can be derived from the translation of RNA or synthesized chemically and can be conjugated to a carrier protein, if desired. Commonly used carriers that are chemically coupled to peptides include bovine serum albumin and thyroglobulin, keyhole limpet hemocyanin. The coupled peptide is then used to immunize the animal (e.g., a mouse, a rat, or a rabbit).

The term "antigenic determinant", as used herein, refers to that fragment of a molecule (i.e., an epitope) that makes contact with a particular antibody. When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The term "antisense", as used herein, refers to any composition containing nucleotide sequences which are complementary to a specific DNA or RNA sequence. The term "antisense strand" is used in reference to a nucleic acid strand that is complementary to the "sense" strand. Antisense molecules include peptide nucleic acids and may be produced by any method including synthesis or transcription. Once introduced into a cell, the complementary nucleotides combine with natural sequences produced by the cell to form duplexes and block either transcription or translation. The designation "negative" is sometimes used in reference to the antisense strand, and "positive" is sometimes used in reference to the sense strand.

The term "biologically active", as used herein, refers to a protein having structural, regulatory, or biochemical functions of a naturally occurring molecule. Likewise, "immunologically active" refers to the capability of the natural, recombinant, or synthetic VTP, or any oligopeptide thereof, to induce a specific immune response in appropriate animals or cells and to bind with specific antibodies.

The terms "complementary" or "complementarity", as used herein, refer to the natural binding of polynucleotides under permissive salt and temperature conditions by base-pairing. For example, the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands and in the design and use of PNA molecules.

A "composition comprising a given polynucleotide sequence" as used herein refers broadly to any composition containing the given polynucleotide sequence. The composition may comprise a dry formulation or an aqueous solution. Compositions comprising polynucleotide sequences encoding VTP (SEQ ID NO:1, SEQ ID NO:3, or SEQ ID NO:5) or fragments thereof (e.g., SEQ ID NO:2, SEQ ID NO:4, SEQ ID NO:6 and fragments thereof) may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., SDS) and other components (e.g., Denhardt's solution, dry milk, salmon sperm DNA, etc.).

"Consensus", as used herein, refers to a nucleic acid sequence which has been resequenced to resolve uncalled bases, has been extended using XL-PCR (Perkin Elmer, Norwalk, Conn.) in the 5' and/or the 3' direction and resequenced, or has been assembled from the overlapping sequences of more than one Incyte Clone using a computer program for fragment assembly (e.g., GELVIEW fragment assembly system, GCG, Madison, Wis.). Some sequences have been both extended and assembled to produce the consensus sequence.

The term "correlates with expression of a polynucleotide", as used herein, indicates that the detection of the presence of ribonucleic acid that is similar to SEQ ID NO:2, SEQ ID NO:4, or SEQ ID NO:6 by northern analysis is indicative of the presence of mRNA encoding VTP in a sample and thereby correlates with expression of the transcript from the polynucleotide encoding the protein.

A "deletion", as used herein, refers to a change in the amino acid or nucleotide sequence and results in the absence of one or more amino acid residues or nucleotides.

The term "derivative", as used herein, refers to the chemical modification of a nucleic acid encoding or complementary to VTP or the encoded VTP. Such modifications include, for example, replacement of hydrogen by an alkyl, acyl, or amino group. A nucleic acid derivative encodes a polypeptide which retains the biological or immunological function of the natural molecule. A derivative polypeptide is one which is modified by glycosylation, pegylation, or any similar process which retains the biological or immunological function of the polypeptide from which it was derived.

The term "homology", as used herein, refers to a degree of complementarity. There may be partial homology or complete homology (i.e., identity). A partially complementary sequence that at least partially inhibits an identical sequence from hybridizing to a target nucleic acid is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or hybridization probe will compete for and inhibit the binding of a completely homologous sequence to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity). In the absence of non-specific binding, the probe will not hybridize to the second non-complementary target sequence.

Human artificial chromosomes (HACs) are linear microchromosomes which may contain DNA sequences of 10K to 10M in size and contain all of the elements required for stable mitotic chromosome segregation and maintenance (Harrington, J. J. et al. (1997) Nat. Genet. 15:345-355).

The term "humanized antibody", as used herein, refers to antibody molecules in which amino acids have been replaced in the non-antigen binding regions in order to more closely resemble a human antibody, while still retaining the original binding ability.

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

An "insertion" or "addition", as used herein, refers to a change in an amino acid or nucleotide sequence resulting in the addition of one or more amino acid residues or nucleotides, respectively, as compared to the naturally occurring molecule.

"Microarray" refers to an array of distinct polynucleotides or oligonucleotides arranged on a substrate, such as paper, nylon or other type of membrane, filter, chip, glass slide, or any other suitable solid support.

The term "modulate", as used herein, refers to a change in the activity of VTP. For example, modulation may cause an increase or a decrease in protein activity, binding characteristics, or any other biological, functional or immunological properties of VTP.

"Nucleic acid sequence" as used herein refers to an oligonucleotide, nucleotide, or polynucleotide, and fragments thereof, and to DNA or RNA of genomic or synthetic origin which may be single- or double-stranded, and represent the sense or antisense strand. "Fragments" are those nucleic acid sequences which are greater than 60 nucleotides than in length, and most preferably includes fragments that are at least 100 nucleotides or at least 1000 nucleotides, and at least 10,000 nucleotides in length.

The term "oligonucleotide" refers to a nucleic acid sequence of at least about 6 nucleotides to about 60 nucleotides, preferably about 15 to 30 nucleotides, and more preferably about 20 to 25 nucleotides, which can be used in PCR amplification or a hybridization assay, or a microarray. As used herein, oligonucleotide is substantially equivalent to the terms "amplimers", "primers", "oligomers", and "probes", as commonly defined in the art.

"Peptide nucleic acid", PNA as used herein, refers to an antisense molecule or anti-gene agent which comprises an oligonucleotide of at least five nucleotides in length linked to a peptide backbone of amino acid residues which ends in lysine. The terminal lysine confers solubility to the composition. PNAs may be pegylated to extend their lifespan in the cell where they preferentially bind complementary single stranded DNA and RNA and stop transcript elongation (Nielsen, P. E. et al. (1993) Anticancer Drug Des. 8:53-63).

The term "portion", as used herein, with regard to a protein (as in "a portion of a given protein") refers to fragments of that protein. The fragments may range in size from five amino acid residues to the entire amino acid sequence minus one amino acid. Thus, for example, a protein "comprising at least a portion of the amino acid sequence of SEQ ID NO:1" encompasses the full-length VTP-1 and fragments thereof.

The term "sample", as used herein, is used in its broadest sense. A biological sample suspected of containing nucleic acid encoding VTP, or fragments thereof, or VTP itself may comprise a bodily fluid, extract from a cell, chromosome, organelle, or membrane isolated from a cell, a cell, genomic DNA, RNA, or cDNA (in solution or bound to a solid support, a tissue, a tissue print, and the like).

The terms "specific binding" or "specifically binding", as used herein, refers to that interaction between a protein or peptide and an agonist, an antibody and an antagonist. The interaction is dependent upon the presence of a particular structure (i.e., the antigenic determinant or epitope) of the protein recognized by the binding molecule. For example, if an antibody is specific for epitope "A", the presence of a protein containing epitope A (or free, unlabeled A) in a reaction containing labeled "A" and the antibody will reduce the amount of labeled A bound to the antibody.

The terms "stringent conditions" or "stringency", as used herein, refer to the conditions for hybridization as defined by the nucleic acid, salt, and temperature. These conditions are well known in the art and may be altered in order to identify or detect identical or related polynucleotide sequences. Numerous equivalent conditions comprising either low or high stringency depend on factors such as the length and nature of the sequence (DNA, RNA, base composition), nature of the target (DNA, RNA, base composition), milieu (in solution or immobilized on a solid substrate), concentration of salts and other components (e.g., formamide, dextran sulfate and/or polyethylene glycol), and temperature of the reactions (within a range from about 5° C. below the melting temperature of the probe to about 20° C. to 25° C. below the melting temperature). One or more factors be may be varied to generate conditions of either low or high stringency different from, but equivalent to, the above listed conditions.

The term "substantially purified", as used herein, refers to nucleic or amino acid sequences that are removed from their natural environment, isolated or separated, and are at least 60% free, preferably 75% free, and most preferably 90% free from other components with which they are naturally associated.

A "substitution", as used herein, refers to the replacement of one or more amino acids or nucleotides by different amino acids or nucleotides, respectively.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the type of host cell being transformed and may include, but is not limited to, viral infection, electroporation, heat shock, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

A "variant" of VTP, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Analogous minor variations may also include amino acid deletions or insertions, or both. Guidance in determining which amino acid residues may be substituted, inserted, or deleted without abolishing biological or immunological activity may be found using computer programs well known in the art, for example, DNASTAR software.

The Invention

The invention is based on the discovery of three new human vesicle trafficking proteins (hereinafter collectively referred to as "VIP"), the polynucleotides encoding VTP, and the use of these compositions for the diagnosis, prevention, or treatment of inflammation and disorders associated with cell proliferation and apoptosis.

Nucleic acids encoding the VTP-1 of the present invention were first identified in Incyte Clone 75871 from a THP-1 cell line cDNA library (THP1PEB01) using a computer search for amino acid sequence alignments. A consensus sequence, SEQ ID NO:2, was derived from the following overlapping and/or extended nucleic acid sequences: Incyte Clones 1396925 (BRAITUT08), 100797 (ADRENOT01), and 75871 (THP1PEB01).

Figure 3B:
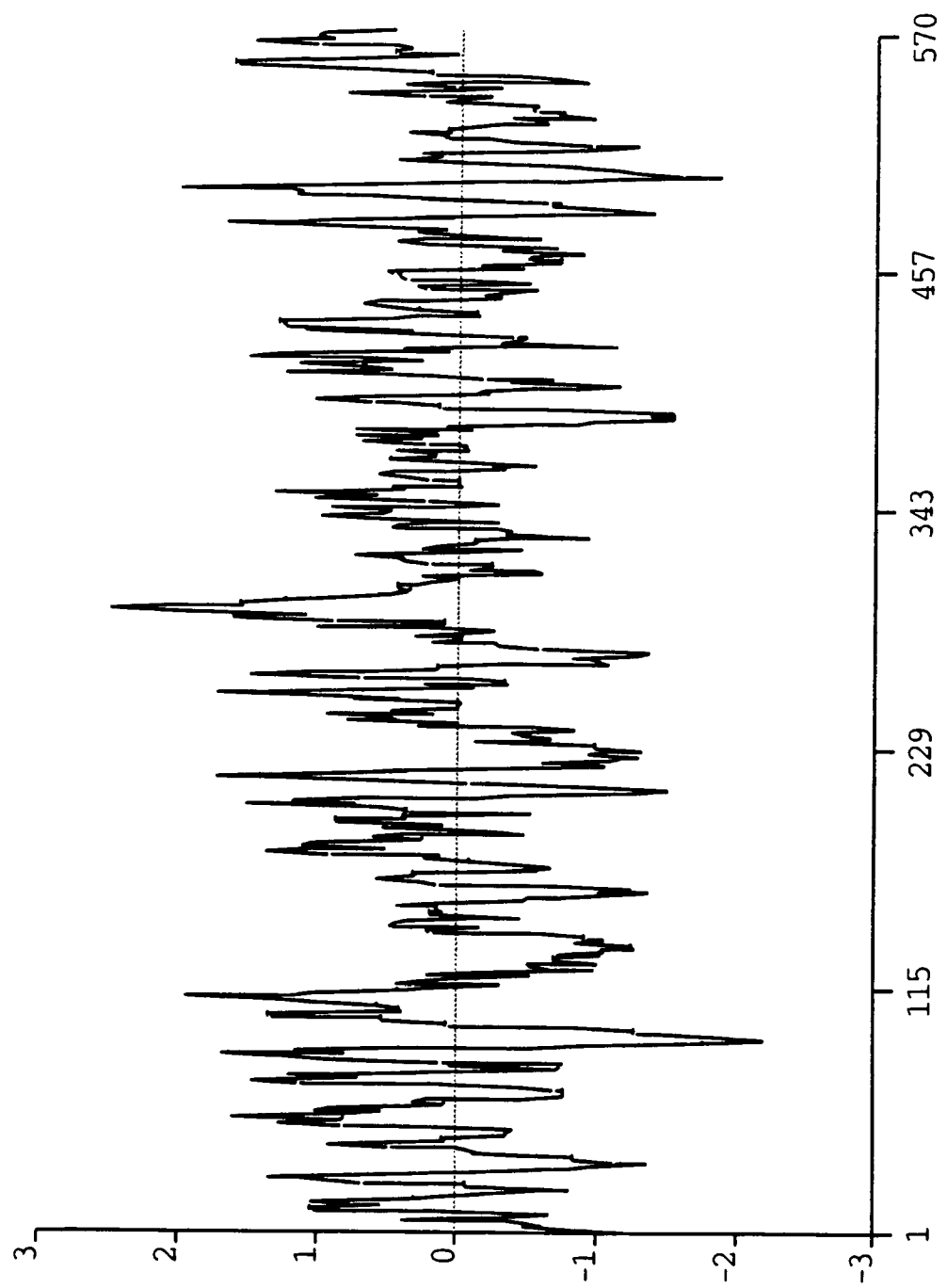

In one embodiment, the invention encompasses a polypeptide, VTP-1, comprising the amino acid sequence of SEQ ID NO:1, as shown in FIGS. 1A, 1B, 1C, 1D, 1E, 1F, and 1G. VTP-1 is 570 amino acids in length. VTP-1 has one potential amidation site encompassing residues G430-R433; one potential N-glycosylation sites encompassing residues N522-T525; one potential cAMP- and cGMP-dependent protein kinase phosphorylation site encompassing residues K322-S325; 10 potential casein kinase II phosphorylation sites encompassing residues T40-E43, S103-D106, S109-E112, S307-D310, S351-E354, T380-D383, S441-D444, T494-D497, T511-E514, and S542-E545; and seven potential protein kinase C phosphorylation sites encompassing residues S168-K170, S343-R345, S416-K418, S441-K443, T494-R496, T563-R565, and S568-R570. As shown in FIGS. 2A and 2B, VTP-1 has chemical and structural homology with a mouse vacuolar protein-sorting protein, mVps45 (GI 1703494; SEQ ID NO:7). In particular, VTP-1 and mVps45 share 97% sequence homology. As illustrated by FIGS. 3A and 3B, VTP-1 and Vps45 have rather similar hydrophobicity plots. Northern analysis shows the expression of VTP-1 in various cDNA libraries, at least 42% of which are immortalized or cancerous, at least 24% of which involve immune response, and at least 29% are expressed in fetal/infant tissues or organs.

Figure 6A:
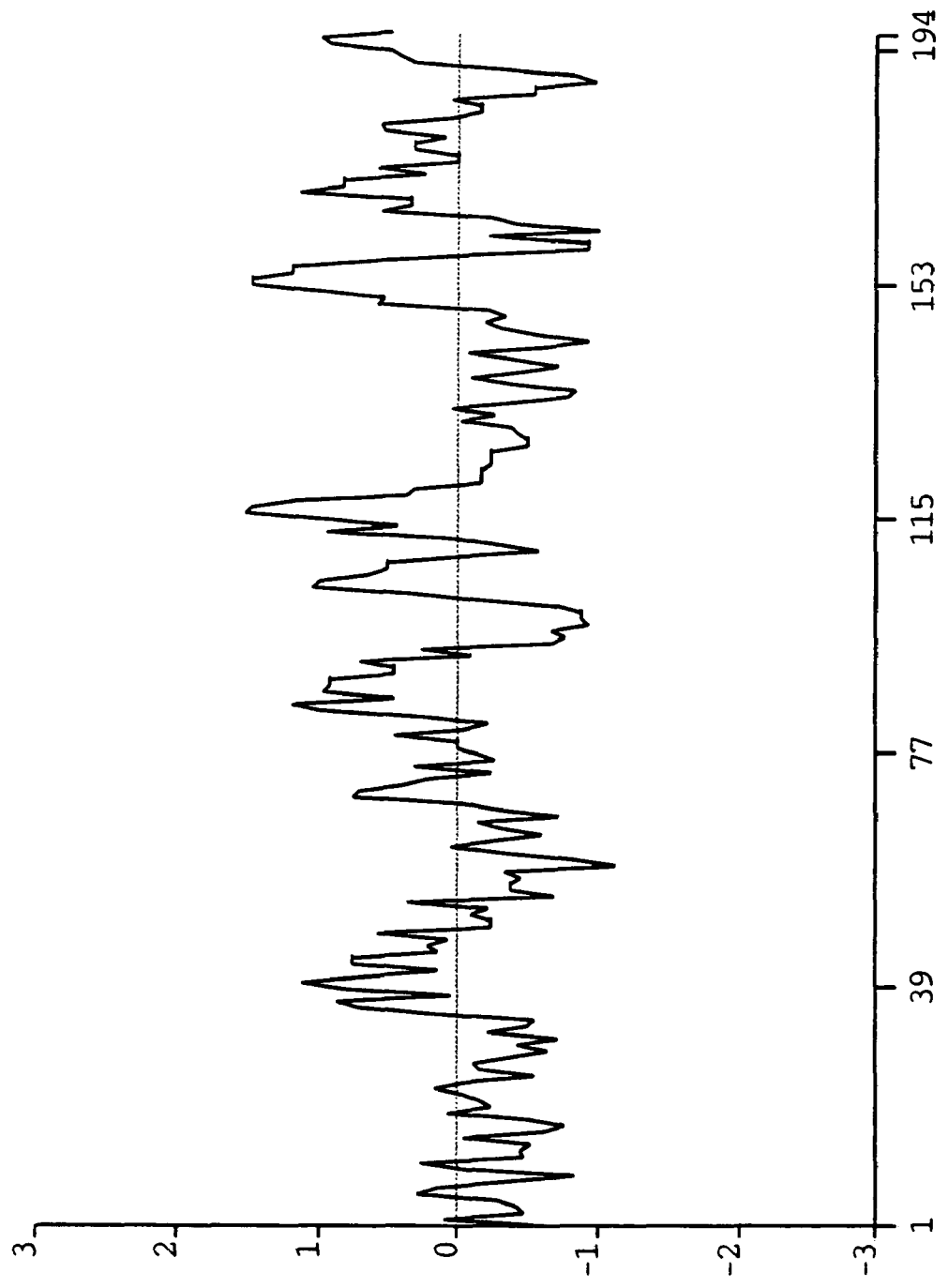
FIGS. 6A and 6B show the hydrophobicity plots for VTP-2 (SEQ ID NO: 3) and px19 (SEQ ID NO:8), respectively. The positive X axis reflects amino acid position, and the negative Y axis, hydrophobicity (MACDNASIS PRO software).
Figure 6B:
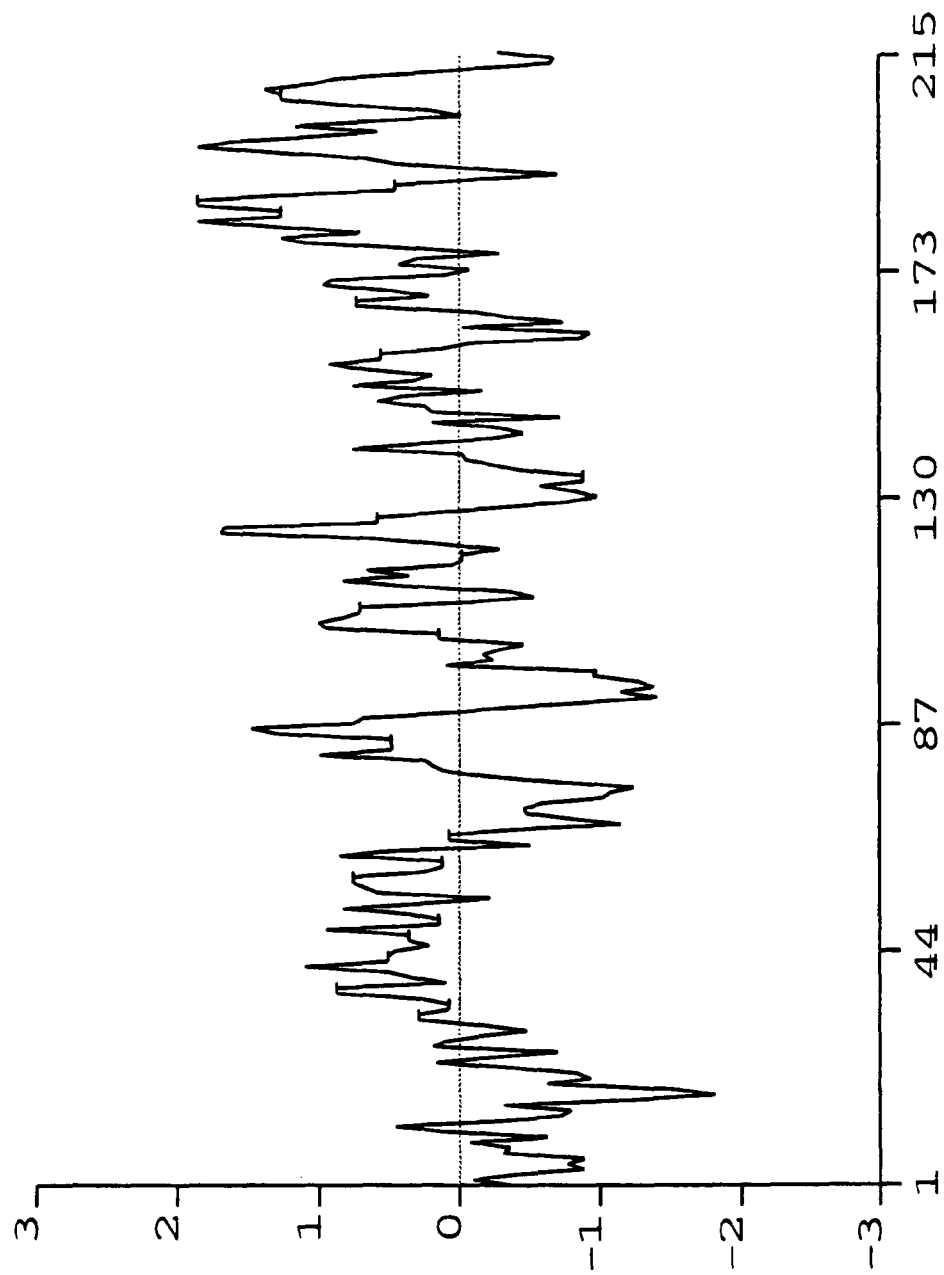

Nucleic acids encoding the VTP-2 of the present invention were first identified in Incyte Clone 2056691 from a bronchial epithelium (NHBE) primary cell line cDNA library (BEPINOT01) using a computer search for amino acid sequence alignments. A consensus sequence, SEQ ID NO:4, was derived from the following overlapping and/or extended nucleic acid sequences: Incyte Clones 3134946 (SMCCNOT01), 744141 (BRSTTUT14), 1610805 (COLNTUT06), and 2056691 (BEPINOT01):

In one embodiment, the invention encompasses a polypeptide, VTP-2, comprising the amino acid sequence of SEQ ID NO:3, as shown in FIGS. 4A, 4B, and 4C. VTP-2 is 194 amino acids in length. VTP-2 has two potential N-glycosylation sites encompassing residues N77-F100 and N152-K155; three potential casein kinase II phosphorylation sites encompassing residues S82-D85, S105-E108, and S139-E142; and five potential protein kinase C phosphorylation sites encompassing residues S46-K48, S51-R53, T131-K133, S177-R179, and T181-R183. As shown in FIG. 5, VTP-2 has chemical and structural homology with an avian homolog of AP small chains, px19 (GI 969170; SEQ ID NO:8). In particular, VTP-2 and px19 share 26% sequence homology. As illustrated by FIGS. 6A and 6B, VTP-2 and px19 have rather similar hydrophobicity plots. Northern analysis shows the expression of VTP-2 in various cDNA libraries, at least 50% of which are immortalized or cancerous, at least 29% of which involve immune response, and at least 11% are expressed in fetal/infant tissues or organs.

Nucleic acids encoding the VTP-3 of the present invention were first identified in Incyte Clone 3086794 from an aortic tissue cDNA library (HEAONOT03) using a computer search for amino acid sequence alignments. A consensus sequence, SEQ ID NO:6, was derived from the following overlapping and/or extended nucleic acid sequences: Incyte Clones 1726 (U937NOT01), 84046 (HYPONOB01), 1441165 (THYRNOT03), 2159212 (ENDCNOT02), 1440158 (THYRNOT03), 1513526 (PANCTUT01), and 3086794 (HEAONOT03).

Figure 9A:
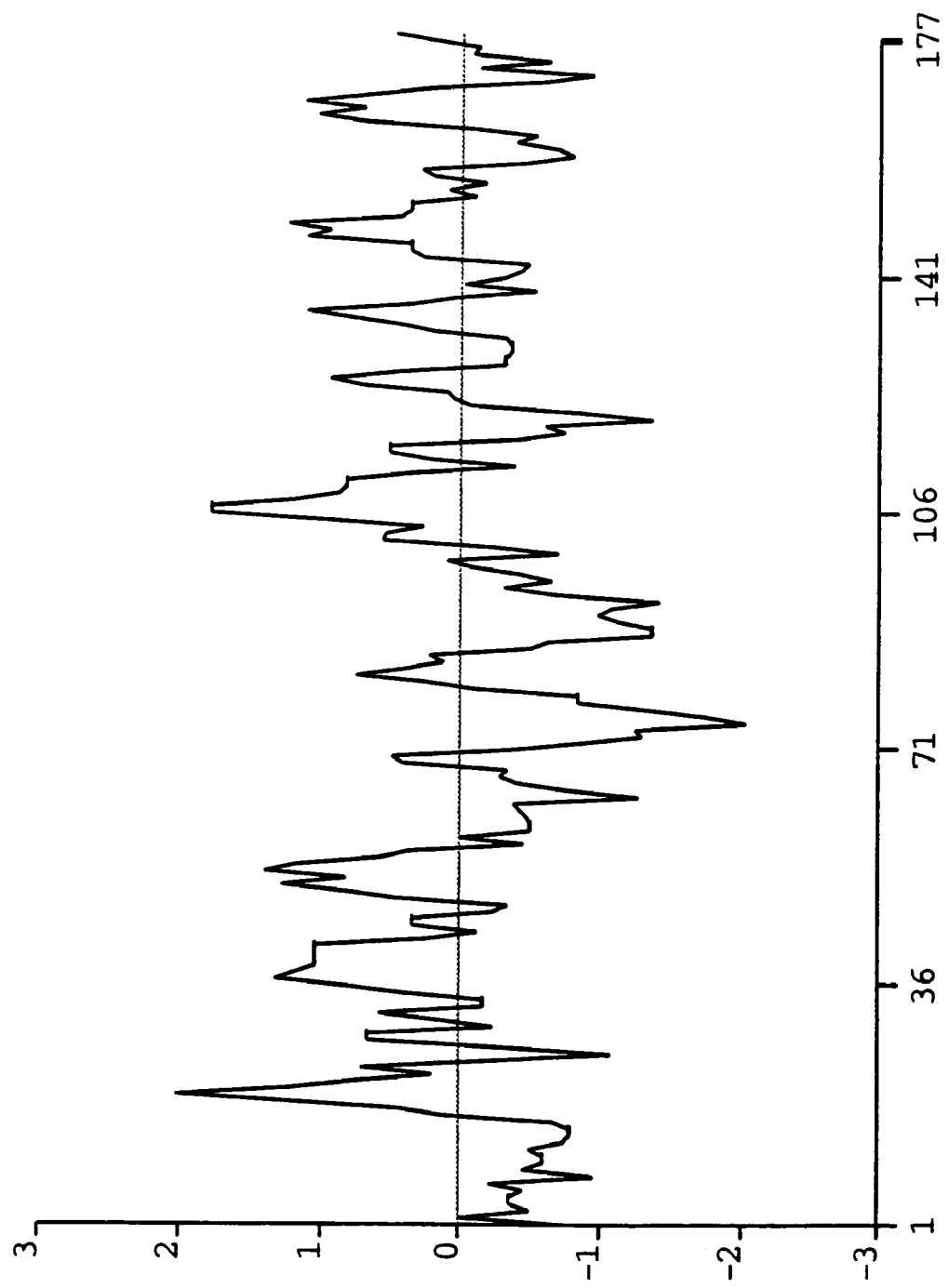
FIGS. 9A and 9B show the hydrophobicity plots for VTP-3 (SEQ ID NO: 5) and ζCOP (SEQ ID NO:9), respectively. The positive X axis reflects amino acid position, and the negative Y axis, hydrophobicity (MACDNASIS PRO software).
Figure 9B:
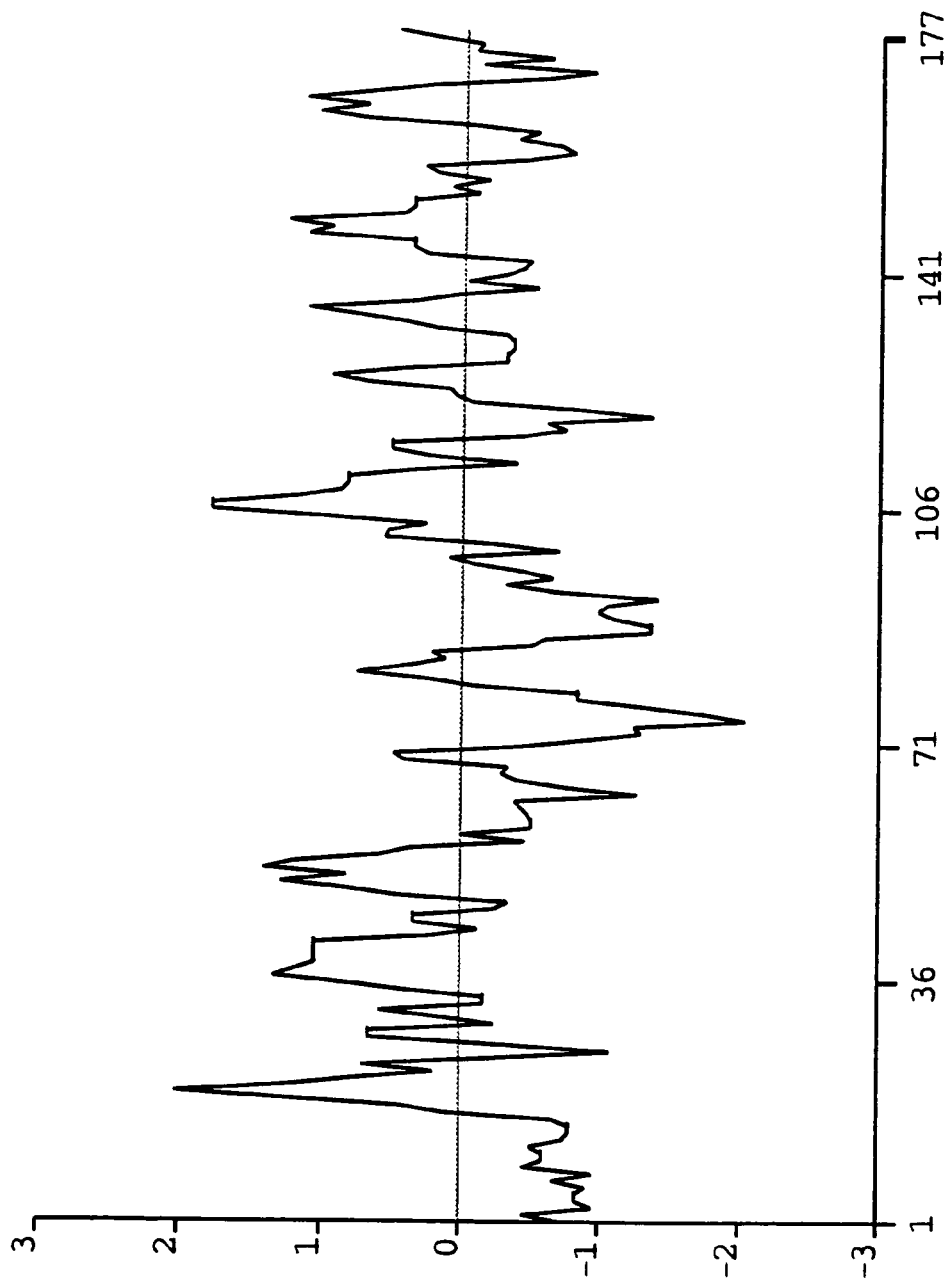

In one embodiment, the invention encompasses a polypeptide, VTP-3, comprising the amino acid sequence of SEQ ID NO:5, as shown in FIGS. 7A, 7B, 7C, 7D, 7E, and 7F. VTP-3 is 177 amino acids in length. It has one potential small chain signature of clathrin adaptor complexes encompassing residues V67-F77. VTP-3 has one potential N-glycosylation site encompassing residues N50-H53; five potential casein kinase II phosphorylation sites encompassing residues S37-E40, T55-E58, S71-D74, S82-E85, and S166-E169; four potential protein kinase C phosphorylation sites encompassing residues T12-K14, S37-K37, T52-R54, and S166-K168; and two potential tyrosine kinase phosphorylation sites encompassing residues K29-Y35 and K70-Y78. As shown in FIG. 8, VTP-3 has chemical and structural homology with a subunit of a cow coatomer, ζCOP (GI 441-486; SEQ ID NO:9). In particular, VTP-3 and ζCOP share 98% sequence homology. As illustrated by FIGS. 9A and 9B, VTP-3 and ζCOP have rather similar hydrophobicity plots. Northern analysis shows the expression of VTP-3 in various cDNA libraries, at least 44% of which are immortalized or cancerous, at least 25% of which involve immune response, and at least 24% are expressed in fetal/infant tissues or organs.

The invention also encompasses VTP variants. A preferred VTP variant is one having at least 80%, and more preferably at least 90%, amino acid sequence identity to the VTP amino acid sequence (SEQ ID NO:1, SEQ ID NO:3, or SEQ ID NO:5) and which retains at least one biological, immunological or other functional characteristic or activity of VTP. A most preferred VTP variant is one having at least 95% amino acid sequence identity to SEQ ID NO:1, SEQ ID NO:3, or SEQ ID NO:5.

The invention also encompasses polynucleotides which encode VTP. Accordingly, any nucleic acid sequence which encodes the amino acid sequence of VTP can be used to produce recombinant molecules which express VTP. In a particular embodiment, the invention encompasses the polynucleotide comprising the nucleic acid sequence of SEQ ID NO:2, SEQ ID NO:4, or SEQ ID NO:6 as shown, respectively, in FIGS. 1A, 1B, 1C, 1D, 1E, 1F, and 1G; FIGS. 4A, 4B, and 4C; or FIGS. 7A, 7B, 7C, 7D, 7E, and 7F.

It will be appreciated by those skilled in the art that as a result of the degeneracy of the genetic code, a multitude of nucleotide sequences encoding VTP, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring VTP, and all such variations are to be considered as being specifically disclosed.

Although nucleotide sequences which encode VTP and its variants are preferably capable of hybridizing to the nucleotide sequence of the naturally occurring VTP under appropriately selected conditions of stringency, it may be advantageous to produce nucleotide sequences encoding VTP or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding VTP and its derivatives without altering the encoded amino acid sequences include the production of RNA transcripts having more desirable properties, such as a greater half-life, than transcripts produced from the naturally occurring sequence.

The invention also encompasses production of DNA sequences, or fragments thereof, which encode VTP and its derivatives, entirely by synthetic chemistry. After production, the synthetic sequence may be inserted into any of the many available expression vectors and cell systems using reagents that are well known in the art. Moreover, synthetic chemistry may be used to introduce mutations into a sequence encoding VTP or any fragment thereof.

Also encompassed by the invention are polynucleotide sequences that are capable of hybridizing to the claimed nucleotide sequences, and, in particular, those shown in SEQ ID NO:2, SEQ ID NO:4, or SEQ ID NO:6, under various conditions of stringency as taught in Wahl, G. M. and S. L. Berger (1987; Methods Enzymol. 152:399-407) and Kimmel, A. R. (1987; Methods Enzymol. 152:507-511).

Methods for DNA sequencing which are well known and generally available in the art and may be used to practice any of the embodiments of the invention. The methods may employ such enzymes as the Klenow fragment of DNA polymerase I, SEQUENASE (US Biochemical Corp, Cleveland, Ohio), Taq polymerase (Perkin Elmer), thermostable T7 polymerase (Amersham, Chicago, Ill.), or combinations of polymerases and proofreading exonucleases such as those found in the ELONGASE amplification system marketed by GIBCO/BRL (Gaithersburg; MD). Preferably, the process is automated with machines such as the MICROLAB 2200 (Hamilton, Reno, Nev.), Peltier thermal cycler (PTC200; MJ Research, Watertown, Mass.), and the ABI CATALYST and 373 and 377 DNA sequencers (Perkin Elmer).

The nucleic acid sequences encoding VTP may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318-322). In particular, genomic DNA is first amplified in the presence of primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nucleic Acids Res. 16:8186). The primers may be designed using commercially available software such as OLIGO 4.06 primer analysis software (National Biosciences Inc., Plymouth, Minn.), or another appropriate program, to be 22-30 nucleotides in length, to have a GC content of 50% or more, and to anneal to the target sequence at temperatures about 68°-72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (1991) PCR Methods Applic. 1:111-119). In this method, multiple restriction enzyme digestions and ligations may also be used to place an engineered double-stranded sequence into an unknown fragment of the DNA molecule before performing PCR.

Another method which may be used to retrieve unknown sequences is that of Parker, J. D. et al. (1991; Nucleic Acids Res. 19:3055-3060). Additionally, one may use PCR, nested primers, and PROMOTERFINDER libraries to walk genomic DNA (Clontech, Palo Alto, Calif.). This process avoids the need to screen libraries and is useful in finding intron/exon junctions. When screening for full-length cDNAs, it is preferable to use libraries that have been size-selected to include larger cDNAs. Also, random-primed libraries are preferable, in that they will contain more sequences which contain the 5' regions of genes. Use of a randomly primed library may be especially preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled device camera. Output/light intensity may be converted to electrical signal using appropriate software (e.g. GENOTYPER and SEQUENCE NAVIGATOR, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode VTP may be used in recombinant DNA molecules to direct expression of VTP, fragments or functional equivalents thereof, in appropriate host cells. Due to the inherent degeneracy of the genetic code, other DNA sequences which encode substantially the same or a functionally equivalent amino acid sequence may be produced, and these sequences may be used to clone and express VTP.

As will be understood by those of skill in the art, it may be advantageous to produce VTP-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences of the present invention can be engineered using methods generally known in the art in order to alter VTP encoding sequences for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, introduce mutations, and so forth.

In another embodiment of the invention, natural, modified, or recombinant nucleic acid sequences encoding VTP may be ligated to a heterologous sequence to encode a fusion protein. For example, to screen peptide libraries for inhibitors of VTP activity, it may be useful to encode a chimeric VTP protein that can be recognized by a commercially available antibody. A fusion protein may also be engineered to contain a cleavage site located between the VTP encoding sequence and the heterologous protein sequence, so that VTP may be cleaved and purified away from the heterologous moiety.

In another embodiment, sequences encoding VTP may be synthesized, in whole or in part, using chemical methods well known in the art (see Caruthers, M. H. et al. (1980) Nucl. Acids Res. Symp. Ser. 215-223, Horn, T. et al. (1980) Nucl. Acids Res. Symp. Ser. 225-232). Alternatively, the protein itself may be produced using chemical methods to synthesize the amino acid sequence of VTP, or a fragment thereof. For example, peptide synthesis can be performed using various solid-phase techniques (Roberge, J. Y. et al. (1995) Science 269:202-204) and automated synthesis may be achieved, for example, using the ABI 431A peptide synthesizer (Perkin Elmer).

The newly synthesized peptide may be substantially purified by preparative high performance liquid chromatography (e.g., Creighton, T. (1983) *Proteins, Structures and Molecular Principles*, WH Freeman and Co., New York, N.Y.). The composition of the synthetic peptides may be confirmed by amino acid analysis or sequencing (e.g., the Edman degradation procedure; Creighton, supra). Additionally, the amino acid sequence of VTP, or any part thereof, may be altered during direct synthesis and/or combined using chemical methods with sequences from other proteins, or any part thereof, to produce a variant polypeptide.

In order to express a biologically active VTP, the nucleotide sequences encoding VTP or functional equivalents, may be inserted into appropriate expression vector, i.e., a vector which contains the necessary elements for the transcription and translation of the inserted coding sequence.

Methods which are well known to those skilled in the art may be used to construct expression vectors containing sequences encoding VTP and appropriate transcriptional and translational control elements. These methods include in vitro recombinant DNA techniques, synthetic techniques, and in vivo genetic recombination. Such techniques are described in Sambrook, J. et al. (1989) *Molecular Cloning, A Laboratory Manual*, Cold Spring Harbor Press, Plainview, N.Y., and Ausubel, F. M. et al. (1989) *Current Protocols in Molecular Biology*, John Wiley & Sons, New York, N.Y.

A variety of expression vector/host systems may be utilized to contain and express sequences encoding VTP. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems. The invention is not limited by the host cell employed.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, LaJolla, Calif.) or PSPORT1 plasmid (Gibco BRL) and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding VTP, vectors based on SV40 or EBV may be used with an appropriate selectable marker.

In bacterial systems, a number of expression vectors may be selected depending upon the use intended for VTP. For example, when large quantities of VTP are needed for the induction of antibodies, vectors which direct high level expression of fusion proteins that are readily purified may be used. Such vectors include, but are not limited to, the multifunctional *E. coli* cloning and expression vectors such as BLUESCRIPT (Stratagene), in which the sequence encoding VTP may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264:5503-5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH may be used. For reviews, see Ausubel et al. (supra) and Grant et al. (1987) Methods Enzymol. 153:516-544.

In cases where plant expression vectors are used, the expression of sequences encoding VTP may be driven by any of a number of promoters. For example, viral promoters such as the 35S and 19S promoters of CaMV may be used alone or in combination with the omega leader sequence from TMV (Takamatsu, N. (1987) EMBO J. 6:307-311). Alternatively, plant promoters such as the small subunit of RUBISCO or heat shock promoters may be used (Coruzzi, G. et al. (1984) EMBO J. 3:1671-1680; Broglie, R. et al. (1984) Science 224:838-843; and Winter, J. et al. (1991) Results Probl. Cell Differ. 17:85-105). These constructs can be introduced into plant cells by direct DNA transformation or pathogen-mediated transfection. Such techniques are described in a number of generally available reviews (see, for example, Hobbs, S. or Murry, L. E. in McGraw Hill *Yearbook of Science and Technology* (1992) McGraw Hill, New York, N.Y.; pp. 191-196.

An insect system may also be used to express VTP. For example, in one such system, *Autographa californica* nuclear polyhedrosis virus (AcNPV) is used as a vector to express foreign genes in *Spodoptera frugiperda* cells or in *Trichoplusia larvae*. The sequences encoding VTP may be cloned into a non-essential region of the virus, such as the polyhedrin gene, and placed under control of the polyhedrin promoter. Successful insertion of VTP will render the polyhedrin gene inactive and produce recombinant virus lacking coat protein. The recombinant viruses may then be used to infect, for example, *S. frugiperda* cells or *Trichoplusia larvae* in which VTP may be expressed (Engelhard, E. K. et al. (1994) Proc. Nat. Acad. Sci. 91:3224-3227).

In mammalian host cells, a number of viral-based expression systems may be utilized. In cases where an adenovirus is used as an expression vector, sequences encoding VTP may be ligated into an adenovirus transcription/translation complex consisting of the late promoter and tripartite leader sequence. Insertion in a non-essential E1 or E3 region of the viral genome may be used to obtain a viable virus which is capable of expressing VTP in infected host cells (Logan, J. and Shenk, T. (1984) Proc. Natl. Acad. Sci. 81:3655-3659). In addition, transcription enhancers, such as the Rous sarcoma virus (RSV) enhancer, may be used to increase expression in mammalian host cells.

Human artificial chromosomes (HACs) may also be employed to deliver larger fragments of DNA than can be contained and expressed in a plasmid. HACs of 6 to 10M are constructed and delivered via conventional delivery methods (liposomes, polycationic amino polymers, or vesicles) for therapeutic purposes.

Specific initiation signals may also be used to achieve more efficient translation of sequences encoding VTP. Such signals include the ATG initiation codon and adjacent sequences. In cases where sequences encoding VTP, its initiation codon, and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125-162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells which have specific cellular machinery and characteristic mechanisms for post-translational activities (e.g., CHO, HeLa, MDCK, HEK293, and WI38), are available from the American Type Culture Collection (ATCC; Bethesda, Md.) and may be chosen to ensure the correct modification and processing of the foreign protein.

For long-term, high-yield production of recombinant proteins, stable expression is preferred. For example, cell lines which stably express VTP may be transformed using expression vectors which may contain viral origins of replication and/or endogenous expression elements and a selectable marker gene on the same or on a separate vector. Following the introduction of the vector, cells may be allowed to grow for 1-2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11:223-32) and adenine phosphoribosyltransferase (Lowy, I. et al. (1980) Cell 22:817-23) genes which can be employed in $tk^-$ or $aprt^-$ cells, respectively. Also, antimetabolite, antibiotic or herbicide resistance can be used as the basis for selection; for example, dhfr, which confers resistance to methotrexate (Wigler, M. et al. (1980) Proc. Natl. Acad. Sci. 77:3567-70); npt, which confers resistance to the aminoglycosides neomycin and G-418 (Colbere-Garapin, F. et al (1981) J. Mol. Biol. 150:1-14) and als or pat, which confer resistance to chlorsulfuron and phosphinothricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:8047-51). Recently, the use of visible markers has gained popularity with such markers as anthocyanins, β glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121-131).

Although the presence/absence of marker gene expression suggests that the gene of interest is also present, its presence and expression may need to be confirmed. For example, if the sequence encoding VTP is inserted within a marker gene sequence, transformed cells containing sequences encoding VTP can be identified by the absence of marker gene function. Alternatively, a marker gene can be placed in tandem with a sequence encoding VTP under the control of a single promoter. Expression of the marker gene in response to induction or selection usually indicates expression of the tandem gene as well.

Alternatively, host cells which contain the nucleic acid sequence encoding VTP and express VTP may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein.

The presence of polynucleotide sequences encoding VTP can be detected by DNA-DNA or DNA-RNA hybridization or amplification using probes or fragments or fragments of polynucleotides encoding VTP. Nucleic acid amplification based assays involve the use of oligonucleotides or oligomers based on the sequences encoding VTP to detect transformants containing DNA or RNA encoding VTP.

A variety of protocols for detecting and measuring the expression of VTP, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on VTP is preferred, but a competitive binding assay may be employed. These and other assays are described, among other places, in Hampton, R. et al. (1990; *Serological Methods, a Laboratory Manual*, APS Press, St Paul, Minn.) and Maddox, D. E. et al. (1983; J. Exp. Med. 158:1211-1216).

A wide variety of labels and conjugation techniques are known by those skilled in the art and may be used in various nucleic acid and amino acid assays. Means for producing labeled hybridization or PCR probes for detecting sequences related to polynucleotides encoding VTP include oligolabeling, nick translation, end-labeling or PCR amplification using a labeled nucleotide. Alternatively, the sequences encoding VTP, or any fragments thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (Pharmacia & Upjohn, (Kalamazoo, Mich.); Promega (Madison, Wis.); and U.S. Biochemical Corp. (Cleveland, Ohio). Suitable reporter molecules or labels, which may be used for ease of detection, include radionuclides, enzymes, fluorescent, chemiluminescent, or chromogenic agents as well as substrates, cofactors, inhibitors, magnetic particles, and the like.

Host cells transformed with nucleotide sequences encoding VTP may be cultured under conditions suitable for the expression and recovery of the protein from cell culture. The protein produced by a transformed cell may be secreted or contained intracellularly depending on the sequence and/or the vector used. As will be understood by those of skill in the art, expression vectors containing polynucleotides which encode VTP may be designed to contain signal sequences which direct secretion of VTP through a prokaryotic or eukaryotic cell membrane. Other constructions may be used to join sequences encoding VTP to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAG extension/affinity purification system (Immunex Corp., Seattle, Wash.). The inclusion of cleavable linker sequences such as those specific for Factor XA or enterokinase (Invitrogen, San Diego, Calif.) between the purification domain and VTP may be used to facilitate purification. One such expression vector provides for expression of a fusion protein containing VTP and a nucleic acid encoding 6 histidine residues preceding a thioredoxin or an enterokinase cleavage site. The histidine residues facilitate purification on IMIAC (immobilized metal ion affinity chromatography) as described in Porath, J. et al. (1992, Prot. Exp. Purif. 3: 263-281) while the enterokinase cleavage site provides a means for purifying VTP from the fusion protein. A discussion of vectors which contain fusion proteins is provided in Kroll, D. J. et al. (1993; DNA Cell Biol. 12:441-453).

In addition to recombinant production, fragments of VTP may be produced by direct peptide synthesis using solid-phase techniques (Merrifield J. (1963) J. Am. Chem. Soc. 85:2149-2154). Protein synthesis may be performed using manual techniques or by automation. Automated synthesis may be achieved, for example, using an Applied Biosystems 431A peptide synthesizer (Perkin Elmer). Various fragments of VTP may be chemically synthesized separately and combined using chemical methods to produce the full length molecule.

Therapeutics

Chemical and structural homology exists between VTP-1 and a mouse vacuolar protein-sorting protein, mVps45 (GI 1703494; SEQ ID NO:7); between VTP-2 and a mouse homolog of AP small chains, px19 (GI 969170; SEQ ID NO:8); and between VTP-3 and a subunit of a cow coatomer, ζCOP (GI 441-486; SEQ ID NO:9). Northern analysis shows that the expression of VTP (SEQ ID NO:1, SEQ ID NO:3, or SEQ ID NO:5) is associated with cancer, inflammation, and fetal/infant development. Therapeutic uses for all three polypeptides are described collectively below.

During fetal development, decreased expression of VTP may cause an increase in apoptosis with no adverse effects to the subject. However, in other situations and in adults, decreased expression of VTP may cause an increase in apoptosis which is detrimental. Therefore, in one embodiment, VTP or a fragment or derivative thereof may be administered to a subject to prevent or treat a disorder associated with an increase in apoptosis. Such disorders include, but are not limited to, AIDS and other infectious or genetic immunodeficiencies, neurodegenerative diseases such as Alzheimer's disease, Parkinson's disease, amyotrophic lateral sclerosis, retinitis pigmentosa, and cerebellar degeneration, myelodysplastic syndromes such as aplastic anemia, ischemic injuries such as myocardial infarction, stroke, and reperfusion injury, toxin-induced diseases such as alcohol-induced liver damage, cirrhosis, and lathyrism, wasting diseases such as cachexia, viral infections such as those caused by hepatitis B and C, and osteoporosis.

In another embodiment, a pharmaceutical composition comprising VTP may be administered to a subject to prevent or treat a disorder associated with increased apoptosis including, but not limited to, those listed above.

In still another embodiment, an agonist which is specific for VTP may be administered to prevent or treat a disorder associated with increased apoptosis including, but not limited to, those listed above.

In still another embodiment, a vector capable of expressing VTP, or a fragment or a derivative thereof, may be used to prevent or treat a disorder associated with increased apoptosis including, but not limited to, those listed above.

In a further embodiment, VTP or a fragment or derivative thereof may be added to cells to stimulate cell proliferation. In particular, VTP may be added to a cell or cells in vivo using delivery mechanisms such as liposomes, viral based vectors, or electroinjection for the purpose of promoting regeneration or cell differentiation of the cell or cells. In addition, VTP may be added to a cell, cell line, tissue or organ culture in vitro or ex vivo to stimulate cell proliferation for use in heterologous or autologous transplantation. In some cases, the cell will have been selected for its ability to fight an infection or a cancer or to correct a genetic defect in a disease such as sickle cell anemia, β thalassemia, cystic fibrosis, or Huntington's chorea.

In another further embodiment, an agonist which is specific for VTP may be administered to a cell to stimulate cell proliferation, as described above.

In another further embodiment, a vector capable of expressing VTP, or a fragment or a derivative thereof, may be administered to a cell or cells in vivo using delivery mechanisms, or to a cell to stimulate cell proliferation, as described above.

Increased expression of VTP appears to be associated with increased cell proliferation. Therefore, in one embodiment, an antagonist of VTP, or a fragment or a derivative thereof, may be administered to a subject to prevent or treat a disorder associated with cell proliferation. Such disorders include various types of cancer including, but not limited to, adenocarcinoma, leukemia, lymphoma, melanoma, myeloma, sarcoma, and teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In one aspect, an antibody specific for VTP may be used directly as an antagonist, or indirectly as a targeting or delivery mechanism for bringing a pharmaceutical agent to cells or tissue which express VTP.

In still another embodiment, a vector expressing the complement of the polynucleotide encoding VTP, or a fragment or a derivative thereof, may be administered to a subject to prevent or treat a disorder associated with cell proliferation including, but not limited to, the types of cancer listed above.

In another embodiment, an antagonist of VTP, or a fragment or a derivative thereof, may be administered to a subject to prevent or treat an inflammation. Disorders associated with inflammation include, but are not limited to, Addison's disease, adult respiratory distress syndrome, allergies, anemia, asthma, atherosclerosis, bronchitis, cholecystitis, Crohn's disease, ulcerative colitis, atopic dermatitis, dermatomyositis, diabetes mellitus, emphysema, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, and autoimmune thyroiditis; complications of cancer, hemodialysis, extracorporeal circulation; viral, bacterial, fungal, parasitic, protozoal, and helminthic infections and trauma. In one aspect, an antibody specific for VTP may be used directly as an antagonist, or indirectly as a targeting or delivery mechanism for bringing a pharmaceutical agent to cells or tissue which express VTP.

In still another embodiment, a vector expressing the complement of the polynucleotide encoding VTP, or a fragment or a derivative thereof, may be administered to a subject to prevent or treat an inflammation associated with any disorder including, but not limited to, those listed above.

In other embodiments, any of the proteins, antagonists, antibodies, agonists, complementary sequences or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of VTP may be produced using methods which are generally known in the art. In particular, purified VTP may be used to produce antibodies or to screen libraries of pharmaceutical agents to identify those which specifically bind VTP.

Antibodies to VTP may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with VTP or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to VTP have an amino acid sequence consisting of at least five amino acids and more preferably at least 10 amino acids. It is also preferable that they are identical to a portion of the amino acid sequence of the natural protein, and they may contain the entire amino acid sequence of a small, naturally occurring molecule. Short stretches of VTP amino acids may be fused with those of another protein such as keyhole limpet hemocyanin and antibody produced against the chimeric molecule.

Monoclonal antibodies to VTP may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) Nature 256:495-497; Kozbor, D. et al. (1985) J. Immunol. Methods 81:31-42; Cote, R. J. et al. (1983) Proc. Natl. Acad. Sci. 80:2026-2030; Cole, S. P. et al. (1984) Mol. Cell Biol. 62:109-120).

In addition, techniques developed for the production of "chimeric antibodies", the splicing of mouse antibody genes to human antibody genes to obtain a molecule with appropriate antigen specificity and biological activity can be used (Morrison, S. L. et al. (1984) Proc. Natl. Acad. Sci. 81:6851-6855; Neuberger, M. S. et al. (1984) Nature 312:604-608; Takeda, S. et al. (1985) Nature 314:452-454). Alternatively, techniques described for the production of single chain antibodies may be adapted, using methods known in the art, to produce VTP-specific single chain antibodies. Antibodies with related specificity, but of distinct idiotypic composition, may be generated by chain shuffling from random combinatorial immunoglobulin libraries (Burton D. R. (1991) Proc. Natl. Acad. Sci. 88:11120-3).

Antibodies may also be produced by inducing in vivo production in the lymphocyte population or by screening immunoglobulin libraries or panels of highly specific binding reagents as disclosed in the literature (Orlandi, R. et al. (1989) Proc. Natl. Acad. Sci. 86: 3833-3837; Winter, G. et al. (1991) Nature 349:293-299).

Antibody fragments which contain specific binding sites for VTP may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse, W. D. et al. (1989) Science 254: 1275-1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between VTP and its specific antibody. A two-site, monoclonal-based immunoassay utilizing monoclonal antibodies reactive to two non-interfering VTP epitopes is preferred, but a competitive binding assay may also be employed (Maddox, supra).

In another embodiment of the invention, the polynucleotides encoding VTP, or any fragment or complement thereof, may be used for therapeutic purposes. In one aspect, the complement of the polynucleotide encoding VTP may be used in situations in which it would be desirable to block the transcription of the mRNA. In particular, cells may be transformed with sequences complementary to polynucleotides encoding VTP. Thus, complementary molecules or fragments may be used to modulate VTP activity, or to achieve regulation of gene function. Such technology is now well known in the art, and sense or antisense oligonucleotides or larger fragments, can be designed from various locations along the coding or control regions of sequences encoding VTP.

Expression vectors derived from retro viruses, adenovirus, herpes or vaccinia viruses, or from various bacterial plasmids may be used for delivery of nucleotide sequences to the targeted organ, tissue or cell population. Methods which are well known to those skilled in the art can be used to construct vectors which will express nucleic acid sequence which is complementary to the polynucleotides of the gene encoding VTP. These techniques are described both in Sambrook et al. (supra) and in Ausubel et al. (supra).

Genes encoding VTP can be turned off by transforming a cell or tissue with expression vectors which express high levels of a polynucleotide or fragment thereof which encodes VTP. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector and even longer if appropriate replication elements are part of the vector system.

As mentioned above, modifications of gene expression can be obtained by designing complementary sequences or antisense molecules (DNA, RNA, or PNA) to the control, 5' or regulatory regions of the gene encoding VTP (signal sequence, promoters, enhancers, and introns). Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, *Molecular and Immunologic Approaches*, Futura Publishing Co., Mt. Kisco, N.Y.). The complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding VTP.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding VTP. Such DNA sequences may be incorporated into a wide variety of vectors with suitable RNA polymerase promoters such as T7 or SP6. Alternatively, these cDNA constructs that synthesize complementary RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections or polycationic amino polymers (Goldman, C. K. et al. (1997) Nature Biotechnology 15:462-66; incorporated herein by reference) may be achieved using methods which are well known in the art.

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of VTP, antibodies to VTP, mimetics, agonists, antagonists, or inhibitors of VTP. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers may also be used for delivery. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, succinic acids, etc. Salts tend to be more soluble in aqueous or other protonic solvents than are the corresponding free base forms. In other cases, the preferred preparation may be a lyophilized powder which may contain any or all of the following: 1-50 mM histidine, 0.1%-2% sucrose, and 2-7% mannitol, at a pH range of 4.5 to 5.5, that is combined with buffer prior to use.

After pharmaceutical compositions have been prepared, they can be placed in an appropriate container and labeled for treatment of an indicated condition. For administration of VTP, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example VTP or fragments thereof, antibodies of VTP, agonists, antagonists or inhibitors of VTP, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between toxic and therapeutic effects is the therapeutic index, which can be expressed as the ratio, LD50/ED50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind VTP may be used for the diagnosis of conditions or diseases characterized by expression of VTP, or in assays to monitor patients being treated with VTP, agonists, antagonists or inhibitors. The antibodies useful for diagnostic purposes may be prepared in the same manner as those described above for therapeutics. Diagnostic assays for VTP include methods which utilize the antibody and a label to detect VTP in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring VTP are known in the art and provide a basis for diagnosing altered or abnormal levels of VTP expression. Normal or standard values for VTP expression are established by combining body fluids or cell extracts taken from normal mammalian subjects, preferably human, with antibody to VTP under conditions suitable for complex formation. The amount of standard complex formation may be quantified by various methods, but preferably by photometric, means. Quantities of VTP expressed in subject samples from biopsied tissues are compared with the standard values. Deviation between standard and subject values establishes the parameters for diagnosing disease.

In another embodiment of the invention, the polynucleotides encoding VTP may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of VTP may be correlated with disease. The diagnostic assay may be used to distinguish between absence, presence, and excess expression of VTP, and to monitor regulation of VTP levels during therapeutic intervention.

In one aspect, hybridization with PCR probes which are capable of detecting polynucleotide sequences, including genomic sequences, encoding VTP or closely related molecules, may be used to identify nucleic acid sequences which encode VTP. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding VTP, alleles, or related sequences.

Probes may also be used for the detection of related sequences, and should preferably contain at least 50% of the nucleotides from any of the VTP encoding sequences. The hybridization probes of the subject invention may be DNA or RNA and derived from the nucleotide sequence of SEQ ID NO:2, SEQ ID NO:4, SEQ ID NO:6, or from genomic sequence including promoter, enhancer elements, and introns of the naturally occurring VTP.

Means for producing specific hybridization probes for DNAs encoding VTP include the cloning of nucleic acid sequences encoding VTP or VTP derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as 32P or 35S, or enzymatic labels, such as alkaline phosphatase coupled to the probe via avidin/biotin coupling systems, and the like.

Polynucleotide sequences encoding VTP may be used for the diagnosis of conditions or disorders which are associated with expression of VTP. Examples of such conditions or disorders include, but are not limited to, disorders associated with cell proliferation such as adenocarcinoma, leukemia, lymphoma, melanoma, myeloma, sarcoma, and teratocarcinoma, and particularly, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; disorders with associated inflammation such as Addison's disease, adult respiratory distress syndrome, allergies, anemia, asthma, atherosclerosis, bronchitis, cholecystitis, Crohn's disease, ulcerative colitis, atopic dermatitis, dermatomyositis, diabetes mellitus, emphysema, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, and autoimmune thyroiditis; complications of cancer, hemodialysis, extracorporeal circulation; viral, bacterial, fungal, parasitic, protozoal, and helminthic infections and trauma; disorders with associated apoptosis such as AIDS and other infectious or genetic immunodeficiencies, neurodegenerative diseases such as Alzheimer's disease, Parkinson's disease, amyotrophic lateral sclerosis, retinitis pigmentosa, and cerebellar degeneration, myelodysplastic syndromes such as aplastic anemia, ischemic injuries such as myocardial infarction, stroke, and reperfusion injury, toxin-induced diseases such as alcohol-induced liver damage, cirrhosis, and lathyrism, wasting diseases such as cachexia, viral infections such as those caused by hepatitis B and C, and osteoporosis. The polynucleotide sequences encoding VTP may be used in Southern or northern analysis, dot blot, or other membrane-based technologies; in PCR technologies; or in dipstick, pin, ELISA assays or microarrays utilizing fluids or tissues from patient biopsies to detect altered VTP expression. Such qualitative or quantitative methods are well known in the art.

In a particular aspect, the nucleotide sequences encoding VTP may be useful in assays that detect activation or induction of various cancers, particularly those mentioned above. The nucleotide sequences encoding VTP may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding VTP in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of VTP, a normal or standard profile for expression is established. This may be accomplished by combining body fluids or cell extracts taken from normal subjects, either animal or human, with a sequence, or a fragment thereof, which encodes VTP, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding VTP may involve the use of PCR. Such oligomers may be chemically synthesized, generated enzymatically, or produced in vitro. Oligomers will preferably consist of two nucleotide sequences, one with sense orientation (5'->3') and another with antisense (3'<-5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of VTP include radiolabeling or biotinylating nucleotides, coamplification of a control nucleic acid, and standard curves onto which the experimental results are interpolated (Melby, P. C. et al. (1993) J. Immunol. Methods, 159:235-244; Duplaa, C. et al. (1993) Anal. Biochem. 212:229-236). The speed of quantitation of multiple samples may be accelerated by running the assay in an ELISA format where the oligomer of interest is presented in various dilutions and a spectrophotometric or colorimetric response gives rapid quantitation.

In further embodiments, an oligonucleotide derived from any of the polynucleotide sequences described herein may be used as a target in a microarray. The microarray can be used to monitor the expression level of large numbers of genes simultaneously (to produce a transcript image), and to identify genetic variants, mutations and polymorphisms. This information will be useful in determining gene function, understanding the genetic basis of disease, diagnosing disease, and in developing and monitoring the activity of therapeutic agents In one embodiment, the microarray is prepared and used according to the methods known in the art such as those described in PCT application WO95/11995 (Chee et al.), Lockhart, D. J. et al. (1996; Nat. Biotech. 14: 1675-1680) and Schena, M. et al. (1996; Proc. Natl. Acad. Sci. 93: 10614-10619).

The microarray is preferably composed of a large number of unique, single-stranded nucleic acid sequences, usually either synthetic antisense oligonucleotides or fragments of cDNAs, fixed to a solid support. The oligonucleotides are preferably about 6-60 nucleotides in length, more preferably about 15 to 30 nucleotides in length, and most preferably about 20 to 25 nucleotides in length. For a certain type of microarray, it may be preferable to use oligonucleotides which are only 7 to 10 nucleotides in length. The microarray may contain oligonucleotides which cover the known 5' (or 3') sequence, or may contain sequential oligonucleotides which cover the full length sequence; or unique oligonucleotides selected from particular areas along the length of the sequence. Polynucleotides used in the microarray may be oligonucleotides that are specific to a gene or genes of interest in which at least a fragment of the sequence is known or that are specific to one or more unidentified cDNAs which are common to a particular cell or tissue type or to a normal, developmental, or disease state. In certain situations, it may be appropriate to use pairs of oligonucleotides on a microarray. The pairs will be identical, except for one nucleotide preferably located in the center of the sequence. The second oligonucleotide in the pair (mismatched by one) serves as a control. The number of oligonucleotide pairs may range from 2 to 1,000,000.

In order to produce oligonucleotides to a known sequence for a microarray, the gene of interest is examined using a computer algorithm which starts at the 5' or more preferably at the 3' end of the nucleotide sequence. The algorithm identifies oligomers of defined length that are unique to the gene, have a GC content within a range suitable for hybridization, and lack predicted secondary structure that may interfere with hybridization. In one aspect, the oligomers are synthesized at designated areas on a substrate using a light-directed chemical process. The substrate may be paper, nylon or any other type of membrane, filter, chip, glass slide, or any other suitable solid support.

In one aspect, the oligonucleotides may be synthesized on the surface of the substrate by using a chemical coupling procedure and an ink jet application apparatus, such as that described in PCT application WO95/251116 (Baldeschweiler et al.). In another aspect, a "gridded" array analogous to a dot or slot blot (HYBRIDOT apparatus, GIBCO/BRL) may be used to arrange and link cDNA fragments or oligonucleotides to the surface of a substrate using a vacuum system, thermal, UV, mechanical or chemical bonding procedures. In yet another aspect, an array may be produced by hand or by using available devices, materials, and machines (including Brinkmann multichannel pipettors or robotic instruments) and may contain 8, 24, 96, 384, 1536 or 6144 oligonucleotides, or any other multiple from 2 to 1,000,000 which lends itself to the efficient use of commercially available instrumentation.

In order to conduct sample analysis using the microarrays, polynucleotides are extracted from a biological sample. The biological samples may be obtained from any bodily fluid (blood, urine, saliva, phlegm, gastric juices, etc.), cultured cells, biopsies, or other tissue preparations. To produce probes, the polynucleotides extracted from the sample are used to produce nucleic acid sequences which are complementary to the nucleic acids on the microarray. If the microarray consists of cDNAs, antisense RNAs (aRNA) are appropriate probes. Therefore, in one aspect, mRNA is used to produce cDNA which, in turn and in the presence of fluorescent nucleotides, is used to produce fragment or oligonucleotide aRNA probes. These fluorescently labeled probes are incubated with the microarray so that the probe sequences hybridize to the cDNA oligonucleotides of the microarray. In another aspect, nucleic acid sequences used as probes can include polynucleotides, fragments, and complementary or antisense sequences produced using restriction enzymes, PCR technologies, and Oligolabeling or TRANSPROBE kits (Pharmacia) well known in the area of hybridization technology.

Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray. A detection system may be used to measure the absence, presence, and amount of hybridization for all of the distinct sequences simultaneously. This data may be used for large scale correlation studies or functional analysis of the sequences, mutations, variants, or polymorphisms among samples (Heller, R. A. et al., (1997) Proc. Natl. Acad. Sci. 94:2150-55).

In another embodiment of the invention, the nucleic acid sequences which encode VTP may also be used to generate hybridization probes which are useful for mapping the naturally occurring genomic sequence. The sequences may be mapped to a particular chromosome, to a specific region of a chromosome or to artificial chromosome constructions, such as human artificial chromosomes (HACs), yeast artificial chromosomes (YACs), bacterial artificial chromosomes (BACs), bacterial P1 constructions or single chromosome cDNA libraries as reviewed in Price, C. M. (1993) Blood Rev. 7:127-134, and Trask, B. J. (1991) Trends Genet. 7:149-154.

Fluorescent in situ hybridization (FISH as described in Verma et al. (1988) *Human Chromosomes: A Manual of Basic Techniques*, Pergamon Press, New York, N.Y.) may be correlated with other physical chromosome mapping techniques and genetic map data. Examples of genetic map data can be found in various scientific journals or at Online Mendelian Inheritance in Man (OMIM). Correlation between the location of the gene encoding VTP on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22-23 (Gatti, R. A. et al. (1988) Nature 336:577-580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, VTP, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between VTP and the agent being tested, may be measured.

Another technique for drug screening which may be used provides for high throughput screening of compounds having suitable binding affinity to the protein of interest as described in published PCT application WO84/03564. In this method, as applied to VTP large numbers of different small test compounds are synthesized on a solid substrate, such as plastic pins or some other surface. The test compounds are reacted with VTP, or fragments thereof, and washed. Bound VTP is then detected by methods well known in the art. Purified VTP can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding VTP specifically compete with a test compound for binding VTP. In this manner, the antibodies can be used to detect the presence of any peptide which shares one or more antigenic determinants with VTP.

In additional embodiments, the nucleotide sequences which encode VTP may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I cDNA Library Construction

The human THP-1 cell line cDNA library, THP1PEB01, was custom-constructed by Stratagene. Poly(A+) RNA (mRNA) was purified from THP-1 cells, and cDNA was synthesized from the mRNA. Synthetic adaptor oligonucleotides were ligated onto cDNA ends enabling its insertion into UNI-ZAP vector system (Stratagene). The custom-constructed library phage particles were transfected into E. coli host strain XL-1BLUE (Stratagene).

The BEPINOT01 cDNA library was constructed from a microscopically normal bronchial epithelium (NHBE) primary cell line derived from a 54-year-old Caucasian male. The frozen tissue was homogenized and lysed using a Polytron PT-3000 homogenizer (Brinkmann Instruments, Westbury, N.Y.) in guanidinium isothiocyanate solution. The lysate was centrifuged over a 5.7 M CsCl cushion using a SW28 rotor in a L8-70M Ultracentrifuge (Beckman Instruments) for 18 hours at 25,000 rpm at ambient temperature. The RNA was extracted with acid phenol pH 4.7, precipitated using 0.3 M sodium acetate and 2.5 volumes of ethanol, resuspended in RNAse-free water, and DNase treated at 37° C. RNA extraction and precipitation were repeated as before. The mRNA was then isolated using the OLIGOTEX kit (QIAGEN) and used to construct the cDNA libraries.

The HEAONOT03 cDNA library was constructed from microscopically normal aorta tissue obtained from a 27-year-old Caucasian female. The frozen tissue was homogenized and lysed in TRIZOL reagent (1 gm tissue/10 ml TRIZOL; Cat. #10296-028; GIBCO/BRL), a monophasic solution of phenol and guanidine isothiocyanate, using a Polytron PT-3000 homogenizer (Brinkmann Instruments). After a brief incubation on ice, chloroform was added (1:5 v/v) and the lysate was centrifuged. The aqueous layer was removed to a fresh tube and the RNA extracted with isopropanol, resuspended in DEPC-treated water, and DNase treated for 25 min at 37° C. The mRNA was re-extracted once with acid phenol-chloroform pH 4.7 and precipitated using 0.3M sodium acetate and 2.5 volumes ethanol. The mRNA was then isolated using the OLIGOTEX kit (QIAGEN, Chatsworth, Calif.) and used to construct the cDNA library.

The mRNA was handled according to the recommended protocols in the SUPERSCRIPT plasmid system for cDNA synthesis and plasmid cloning (Cat. #18248-013, GIBCO/BRL). The cDNAs were fractionated on a SEPHAROSE CL4B column (Cat. #275105-01; Pharmacia), and those cDNAs exceeding 400 by were ligated into PSPORT1 (BEPINOT01) or pINCY 1 (HEAONOT03). The plasmids were subsequently transformed into DH5α competent cells (Cat. #18258-012; GIBCO/BRL).

II Isolation and Sequencing of cDNA Clones

The phagemid forms of individual cDNA clones for THP1PEB01 were obtained by the in vivo excision process, in which the host bacterial strain was coinfected with both the lambda library phage and an f1 helper phage. Proteins derived from both the library-containing phage and the helper phage nicked the lambda DNA, initiated new DNA synthesis from defined sequences on the lambda target DNA and created a smaller, single stranded circular phagemid DNA molecule that included all DNA sequences of the PBLUESCRIPT plasmid and the cDNA insert. The phagemid DNA was secreted from the cells, purified, and used to re-infect fresh host cells where the double-stranded phagemid DNA was produced. Because the phagemid carries the gene for β-lactamase, the newly-transformed bacteria were selected on medium containing ampicillin.

Phagemid DNA was purified using the QIAWELL-8 Plasmid, QIAWELL PLUS, or QIAWELL ULTRA DNA purification system (QIAGEN). The DNA was eluted from the purification resin already prepared for DNA sequencing and other analytical manipulations.

Plasmid cDNA for BEPINOT01 or HEAONOT03 was released from the cells and purified using the R.E.A.L. PREP 96 plasmid kit (Catalog #26173, QIAGEN). This kit enabled the simultaneous purification of 96 samples in a 96-well block using multi-channel reagent dispensers. The recommended protocol was employed except for the following changes: 1) the bacteria were cultured in 1 ml of sterile Terrific Broth (Catalog #22711, GIBCO/BRL) with carbenicillin at 25 mg/L and glycerol at 0.4%; 2) after inoculation, the cultures were incubated for 19 hours and at the end of incubation, the cells were lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4° C.

The cDNAs were sequenced according to the method of Sanger et al. (1975, J. Mol. Biol. 94:4411), using the Perkin Elmer CATALYST 800 or a MICROLAB 2200 (Hamilton, Reno, Nev.) in combination with Peltier thermal cyclers (PTC200 from MJ Research, Watertown, Mass.) and Applied Biosystems 377 DNA sequencing systems or the Perkin Elmer 373 DNA sequencing system and the reading frame was determined.

III Homology Searching of cDNA Clones and their Deduced Proteins

The nucleotide sequences of the Sequence Listing or amino acid sequences deduced from them were used as query sequences against databases such as GenBank, SwissProt, BLOCKS, and Pima II. These databases which contain previously identified and annotated sequences were searched for regions of homology (similarity) using BLAST, which stands for Basic Local Alignment Search Tool (Altschul S F (1993) J. Mol. Evol. 36:290-300; Altschul, S F et al. (1990) J. Mol. Biol. 215:403-10).

BLAST produces alignments of both nucleotide and amino acid sequences to determine sequence similarity. Because of the local nature of the alignments, BLAST is especially useful in determining exact matches or in identifying homologs which may be of prokaryotic (bacterial) or eukaryotic (animal, fungal or plant) origin. Other algorithms such as the one described in Smith R F and T F Smith (1992 Protein Engineering 5:35-51), incorporated herein by reference, can be used when dealing with primary sequence patterns and secondary structure gap penalties. As disclosed in this application, the sequences have lengths of at least 49 nucleotides, and no more than 12% uncalled bases (where N is recorded rather than A, C, G, or T).

The BLAST approach, as detailed in Karlin and Altschul (1993; Proc Nat Acad Sci 90:5873-7) and incorporated herein by reference, searches matches between a query sequence and a database sequence, to evaluate the statistical significance of any matches found, and to report only those matches which satisfy the user-selected threshold of significance. In this application, threshold was set at $10^{-25}$ for nucleotides and $10^{-14}$ for peptides.

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al., supra).

Analogous computer techniques using BLAST (Altschul, S. F. (1993) *J. Mol. Evol.* 36:290-300; Altschul, S. F. et al. (1990) *J. Mol. Evol.* 215:403-410) are used to search for identical or related molecules in nucleotide databases such as GenBank or the LIFESEQ database (Incyte Pharmaceuticals). This analysis is much faster than multiple, membrane-based hybridizations. In addition, the sensitivity of the computer search can be modified to determine whether any particular match is categorized as exact or homologous.

The basis of the search is the product score which is defined as:

$$\frac{\% \text{ sequence identity} \times \% \text{ maximum BLAST score}}{100}$$

The product score takes into account both the degree of similarity between two sequences and the length of the sequence match. For example, with a product score of 40, the match will be exact within a 1-2% error; and at 70, the match will be exact. Homologous molecules are usually identified by selecting those which show product scores between 15 and 40, although lower scores may identify related molecules.

The results of northern analysis are reported as a list of libraries in which the transcript encoding VTP occurs. Abundance and percent abundance are also reported. Abundance directly reflects the number of times a particular transcript is represented in a cDNA library, and percent abundance is abundance divided by the total number of sequences examined in the cDNA library.

V Extension of VTP Encoding Polynucleotides

The nucleic acid sequence of the Incyte Clones 75871, 2056691, or 3086794 was used to design oligonucleotide primers for extending a partial nucleotide sequence to full length. One primer was synthesized to initiate extension in the antisense direction, and the other was synthesized to extend sequence in the sense direction. Primers were used to facilitate the extension of the known sequence "outward" generating amplicons containing new, unknown nucleotide sequence for the region of interest. The initial primers were designed from the cDNA using OLIGO 4.06 software (National Biosciences), or another appropriate program, to be about 22 to about 30 nucleotides in length, to have a GC content of 50% or more, and to anneal to the target sequence at temperatures of about 68° to about 72° C. Any stretch of nucleotides which would result in hairpin structures and primer-primer dimerizations was avoided.

Selected human cDNA libraries (GIBCO/BRL) were used to extend the sequence. If more than one extension is necessary or desired, additional sets of primers are designed to further extend the known region.

High fidelity amplification was obtained by following the instructions for the XL-PCR kit (Perkin Elmer) and thoroughly mixing the enzyme and reaction mix. Beginning with 40 pmol of each primer and the recommended concentrations of all other components of the kit, PCR was performed using the Peltier thermal cycler (PTC200; M.J. Research, Watertown, Mass.) and the following parameters:

| | |
|---|---|
| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat step 4-6 for 15 additional cycles |
| Step 8 | 94 ° C. for 15 sec |
| Step 9 | 65° C. for 1 min |
| Step 10 | 68° C. for 7:15 min |
| Step 11 | Repeat step 8-10 for 12 cycles |
| Step 12 | 72° C. for 8 min |
| Step 13 | 4° C. (and holding) |

A 5-10 µl aliquot of the reaction mixture was analyzed by electrophoresis on a low concentration (about 0.6-0.8%) agarose mini-gel to determine which reactions were successful in extending the sequence. Bands thought to contain the largest products were excised from the gel, purified using QIAQUICK (QIAGEN Inc., Chatsworth, Calif.), and trimmed of overhangs using Klenow enzyme to facilitate religation and cloning.

After ethanol precipitation, the products were redissolved in 13 µl of ligation buffer, 1 µl T4-DNA ligase (15 units) and 1 µl T4 polynucleotide kinase were added, and the mixture was incubated at room temperature for 2-3 hours or overnight at 16° C. Competent *E. coli* cells (in 40 µl of appropriate media) were transformed with 3 µl of ligation mixture and cultured in 80 µl of SOC medium (Sambrook et al., supra). After incubation for one hour at 37° C., the *E. coli* mixture was plated on Luria Bertani (LB)-agar (Sambrook et al., supra) containing 2× Carb. The following day, several colonies were randomly picked from each plate and cultured in 150 µl of liquid LB/2× Carb medium placed in an individual well of an appropriate, commercially-available, sterile 96-well microtiter plate. The following day, 5 µl of each overnight culture was transferred into a non-sterile 96-well plate and after dilution 1:10 with water, 5 µl of each sample was transferred into a PCR array.

For PCR amplification, 18 µl of concentrated PCR reaction mix (3.3×) containing 4 units of rTth DNA polymerase, a vector primer, and one or both of the gene specific primers used for the extension reaction were added to each well. Amplification was performed using the following conditions:

| | |
|---|---|
| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2-4 for an additional 29 cycles |

| | |
|---|---|
| Step 6 | 72° C. for 180 sec |
| Step 7 | 4° C. (and holding) |

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequence of SEQ ID NO:2, SEQ ID NO:4, or SEQ ID NO:6 is used to obtain 5' regulatory sequences using the procedure above, oligonucleotides designed for 5' extension, and an appropriate genomic library.

VI Labeling and Use of Individual Hybridization Probes

Hybridization probes derived from SEQ ID NO:2, SEQ ID NO:4, or SEQ ID NO:6 are employed to screen cDNAs, genomic DNAs, or mRNAs. Although the labeling of oligonucleotides, consisting of about 20 base-pairs, is specifically described, essentially the same procedure is used with larger nucleotide fragments. Oligonucleotides are designed using state-of-the-art software such as OLIGO 4.06 software (National Biosciences), labeled by combining 50 pmol of each oligomer and 250 µCi of [γ-$^{32}$P] adenosine triphosphate (Amersham) and T4 polynucleotide kinase (DuPont NEN, Boston, Mass.). The labeled oligonucleotides are substantially purified with SEPHADEX G-25 superfine resin column (Pharmacia & Upjohn). A aliquot containing $10^7$ counts per minute of the labeled probe is used in a typical membrane-based hybridization analysis of human genomic DNA digested with one of the following endonucleases (Ase I, Bgl II, Eco RI, Pst I, Xba I, or Pvu II; DuPont NEN).

The DNA from each digest is fractionated on a 0.7 percent agarose gel and transferred to nylon membranes (NYTRAN PLUS, Schleicher & Schuell, Durham, N.H.). Hybridization is carried out for 16 hours at 40° C. To remove nonspecific signals, blots are sequentially washed at room temperature under increasingly stringent conditions up to 0.1× saline sodium citrate and 0.5% sodium dodecyl sulfate. After XOMAT AR film (Kodak, Rochester, N.Y.) is exposed to the blots, or the blots are exposed in a PhosphorImager cassette (Molecular Dynamics, Sunnyvale, Calif.), hybridization patterns are compared visually.

VII Microarrays

To produce oligonucleotides for a microarray, one of the nucleotide sequences of the present invention are examined using a computer algorithm which starts at the 3' end of the nucleotide sequence. The algorithm identified oligomers of defined length that are unique to the gene, have a GC content within a range suitable for hybridization, and lack predicted secondary structure that would interfere with hybridization. The algorithm identifies approximately 20 sequence-specific oligonucleotides of 20 nucleotides in length (20-mers). A matched set of oligonucleotides are created in which one nucleotide in the center of each sequence is altered. This process is repeated for each gene in the microarray, and double sets of twenty 20 mers are synthesized and arranged on the surface of the silicon chip using a light-directed chemical process, such as that discussed in Chee, supra.

In the alternative, a chemical coupling procedure and an ink jet device are used to synthesize oligomers on the surface of a substrate (cf. Baldeschweiler, supra). In another alternative, a "gridded" array analogous to a dot (or slot) blot is used to arrange and link cDNA fragments or oligonucleotides to the surface of a substrate using a vacuum system, thermal, UV, mechanical or chemical bonding procedures. A typical array may be produced by hand or using available materials and machines and contain grids of 8 dots, 24 dots, 96 dots, 384 dots, 1536 dots or 6144 dots. After hybridization, the microarray is washed to remove nonhybridized probes, and a scanner is used to determine the levels and patterns of fluorescence. The scanned image is examined to determine degree of complementarity and the relative abundance/expression level of each oligonucleotide sequence in the microarray.

VIII Complementary Polynucleotides

Sequence complementary to the VTP-encoding sequence, or any part thereof, is used to decrease or inhibit expression of naturally occurring VTP. Although use of oligonucleotides comprising from about 15 to about 30 base-pairs is described, essentially the same procedure is used with smaller or larger sequence fragments. Appropriate oligonucleotides are designed using OLIGO 4.06 software and the coding sequence of VTP, SEQ ID NO:1, SEQ ID NO:3, or SEQ ID NO:5. To inhibit transcription, a complementary oligonucleotide is designed from the most unique 5' sequence and used to prevent promoter binding to the coding sequence. To inhibit translation, a complementary oligonucleotide is designed to prevent ribosomal binding to the VTP-encoding transcript.

IX Expression of VTP

Expression of VTP is accomplished by subcloning the cDNAs into appropriate vectors and transforming the vectors into host cells. In this case, the cloning vector is also used to express VTP in *E. coli*. Upstream of the cloning site, this vector contains a promoter for β-galactosidase, followed by sequence containing the amino-terminal Met, and the subsequent seven residues of β-galactosidase. Immediately following these eight residues is a bacteriophage promoter useful for transcription and a linker containing a number of unique restriction sites.

Induction of an isolated, transformed bacterial strain with IPTG using standard methods produces a fusion protein which consists of the first eight residues of β-galactosidase, about 5 to 15 residues of linker, and the full length protein. The signal residues direct the secretion of VTP into the bacterial growth media which can be used directly in the following assay for activity.

X Demonstration of VTP Activity

VTP can be expressed by transforming a mammalian cell line such as COST, HeLa or CHO with an eukaryotic expression vector encoding VTP. Eukaryotic expression vectors are commercially available, and the techniques to introduce them into cells are well known to those skilled in the art. The cells are incubated for 48-72 hours after transformation under conditions appropriate for the cell line to allow expression of VTP. Then, phase microscopy is used to compare the mitotic index of transformed versus control cells. An increase in the mitotic index indicates VTP activity.

XI Production of VTP Specific Antibodies

VTP that is substantially purified using PAGE electrophoresis (Sambrook, supra), or other purification techniques, is used to immunize rabbits and to produce antibodies using standard protocols. The amino acid sequence deduced from SEQ ID NO:2, SEQ ID NO:4, or SEQ ID NO:6 is analyzed using DNASTAR software (DNASTAR Inc.) to determine regions of high immunogenicity and a corresponding oligopeptide is synthesized and used to raise antibodies by means known to those of skill in the art. Selection of appropriate epitopes, such as those near the C-terminus or in hydrophilic regions, is described by Ausubel et al. (supra), and others.

Typically, the oligopeptides are 15 residues in length, synthesized using an Applied Biosystems 431A peptide synthesizer using fmoc-chemistry, and coupled to keyhole limpet hemocyanin (KLH, Sigma, St. Louis, Mo.) by reaction with N-maleimidobenzoyl-N-hydroxysuccinimide ester (MBS; Ausubel et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radio iodinated, goat anti-rabbit IgG.

XII Purification of Naturally Occurring VTP Using Specific Antibodies

Naturally occurring or recombinant VTP is substantially purified by immunoaffinity chromatography using antibodies specific for VTP. An immunoaffinity column is constructed by covalently coupling VTP antibody to an activated chromatographic resin, such as CNBr-activated SEPHAROSE (Pharmacia & Upjohn). After the coupling, the resin is blocked and washed according to the manufacturer's instructions.

Media containing VTP is passed over the immunoaffinity column, and the column is washed under conditions that allow the preferential absorbance of VTP (e.g., high ionic strength buffers in the presence of detergent). The column is eluted under conditions that disrupt antibody/VTP binding (eg, a buffer of pH 2-3 or a high concentration of a chaotrope, such as urea or thiocyanate ion), and VTP is collected.

XIII Identification of Molecules which Interact with VTP

VTP or biologically active fragments thereof are labeled with $^{125}$I Bolton-Hunter reagent (Bolton et al. (1973) Biochem. J. 133: 529). Candidate molecules previously arrayed in the wells of a multi-well plate are incubated with the labeled VTP, washed and any wells with labeled VTP complex are assayed. Data obtained using different concentrations of VTP are used to calculate values for the number, affinity, and association of VTP with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. An isolated polypeptide comprising an amino acid sequence selected from the group consisting of:
   a) an amino acid sequence selected from the group consisting of SEQ ID NO:1, SEQ ID NO:3, and SEQ ID NO:5,
   b) a naturally-occurring amino acid sequence having at least 98% sequence identity to an amino acid sequence selected from the group consisting of SEQ ID NO:1 and SEQ ID NO:3.

2. An isolated polypeptide of claim 1, comprising an amino acid sequence selected from the group consisting of SEQ ID NO:1, SEQ ID NO:3, and SEQ ID NO:5.

3. A composition comprising an a polypeptide of claim 1 and a pharmaceutically acceptable excipient.

4. A composition of claim 3, wherein the polypeptide comprises an amino acid sequence selected from the group consisting of SEQ ID NO:1, SEQ ID NO:3, and SEQ ID NO:5.

5. An isolated polypeptide of claim 1, comprising the amino acid sequence of SEQ ID NO:1.

6. A composition of claim 3, wherein the polypeptide comprises the amino acid sequence of SEQ ID NO:1.

* * * * *

```
                         SEQUENCE LISTING (1) GENERAL INFORMATION:

(iii) NUMBER OF SEQUENCES: 9

(2) INFORMATION FOR SEQ ID NO: 1:

(i) SEQUENCE CHARACTERISTICS:
         (A) LENGTH: 570 amino acids
         (B) TYPE: amino acid
         (C) STRANDEDNESS: single
         (D) TOPOLOGY: linear (vii) IMMEDIATE SOURCE:
         (A) LIBRARY: THPIPEB01
         (B) CLONE: 75871

(xi) SEQUENCE DESCRIPTION: SEQ ID NO: 1:

Met Asn Val Val Phe Ala Val Lys Gln Tyr Ile Ser Lys Met Ile Glu
1               5                  10                  15

Asp Ser Gly Pro Gly Met Lys Val Leu Leu Met Asp Lys Glu Thr Thr
            20                  25                  30

Gly Ile Val Ser Met Val Tyr Thr Gln Ser Glu Ile Leu Gln Lys Glu
        35                  40                  45

Val Tyr Leu Phe Glu Arg Ile Asp Ser Gln Asn Arg Glu Ile Met Lys
    50                  55                  60

His Leu Lys Ala Ile Cys Phe Leu Arg Pro Thr Lys Glu Asn Val Asp
65                  70                  75                  80

Tyr Ile Ile Gln Glu Leu Arg Arg Pro Lys Tyr Thr Ile Tyr Phe Ile
                85                  90                  95
```

```
Tyr Phe Ser Asn Val Ile Ser Lys Ser Asp Val Lys Ser Leu Ala Glu
            100                 105                 110

Ala Asp Glu Gln Glu Val Val Ala Glu Val Gln Glu Phe Tyr Gly Asp
        115                 120                 125

Tyr Ile Ala Val Asn Pro His Leu Phe Ser Leu Asn Ile Leu Gly Cys
    130                 135                 140

Cys Gln Gly Arg Asn Trp Asp Pro Ala Gln Leu Ser Arg Thr Thr Gln
145                 150                 155                 160

Gly Leu Thr Ala Leu Leu Leu Ser Leu Lys Lys Cys Pro Met Ile Arg
                165                 170                 175

Tyr Gln Leu Ser Ser Glu Ala Ala Lys Arg Leu Ala Glu Cys Val Lys
                180                 185                 190

Gln Val Ile Thr Lys Glu Tyr Glu Leu Phe Glu Phe Arg Arg Thr Glu
            195                 200                 205

Val Pro Pro Leu Leu Leu Ile Leu Asp Arg Cys Asp Asp Ala Ile Thr
        210                 215                 220

Pro Leu Leu Asn Gln Trp Thr Tyr Gln Ala Met Val His Glu Leu Leu
225                 230                 235                 240

Gly Ile Asn Asn Asn Arg Ile Asp Leu Ser Arg Val Pro Gly Ile Ser
                245                 250                 255

Lys Asp Leu Arg Glu Val Val Leu Ser Ala Glu Asn Asp Glu Phe Tyr
                260                 265                 270

Ala Asn Asn Met Tyr Leu Asn Phe Ala Glu Ile Gly Ser Asn Ile Lys
            275                 280                 285

Asn Leu Met Glu Asp Phe Gln Lys Lys Pro Lys Glu Gln Gln Lys
            290                 295                 300

Leu Glu Ser Ile Ala Asp Met Lys Ala Phe Val Glu Asn Tyr Pro Gln
305                 310                 315                 320

Phe Lys Lys Met Ser Gly Thr Val Ser Lys His Val Thr Val Val Gly
                325                 330                 335

Glu Leu Ser Arg Leu Val Ser Glu Arg Asn Leu Leu Glu Val Ser Glu
                340                 345                 350

Val Glu Gln Glu Leu Ala Cys Gln Asn Asp His Ser Ser Ala Leu Gln
            355                 360                 365

Asn Ile Lys Arg Leu Leu Gln Asn Pro Lys Val Thr Glu Phe Asp Ala
            370                 375                 380

Ala Arg Leu Val Met Leu Tyr Ala Leu His Tyr Glu Arg His Ser Ser
385                 390                 395                 400

Asn Ser Leu Pro Gly Leu Met Met Asp Leu Arg Asn Lys Gly Val Ser
                405                 410                 415

Glu Lys Tyr Arg Lys Leu Val Ser Ala Val Glu Tyr Gly Gly Lys
            420                 425                 430

Arg Val Arg Gly Ser Asp Leu Phe Ser Pro Lys Asp Ala Val Ala Ile
            435                 440                 445

Thr Lys Gln Phe Leu Lys Gly Leu Lys Gly Val Glu Asn Val Tyr Thr
        450                 455                 460

Gln His Gln Pro Phe Leu His Glu Thr Leu Asp His Leu Ile Lys Gly
465                 470                 475                 480

Arg Leu Lys Glu Asn Leu Tyr Pro Tyr Leu Gly Pro Ser Thr Leu Arg
                485                 490                 495

Asp Arg Pro Gln Asp Ile Ile Val Phe Val Ile Gly Gly Ala Thr Tyr
            500                 505                 510

Glu Glu Ala Leu Thr Val Tyr Asn Leu Asn Arg Thr Thr Pro Gly Val
```

```
                515                 520                 525
Arg Ile Val Leu Gly Gly Thr Thr Val His Asn Thr Lys Ser Phe Leu
            530                 535                 540

Glu Glu Val Leu Ala Ser Gly Leu His Ser Arg Ser Lys Glu Ser Ser
545                 550                 555                 560

Gln Val Thr Ser Arg Ser Ala Ser Arg Arg
                565                 570

(2) INFORMATION FOR SEQ ID NO: 2:

(i) SEQUENCE CHARACTERISTICS:
        (A) LENGTH: 2342 base pairs
        (B) TYPE: nucleic acid
        (C) STRANDEDNESS: single
        (D) TOPOLOGY: linear (vii) IMMEDIATE SOURCE:
        (A) LIBRARY: THPIPEB01
        (B) CLONE: 75871

(xi) SEQUENCE DESCRIPTION: SEQ ID NO: 2:

GGACCTCGCG TCGGGCCAAC AGACTGCGGG GTTAATTTAG CCAGACACGT GGGCGGGAAG      60

GGCTGTAGGG TACTTGTCAA TTCGCCGCCA TGAACGTGGT TTTTGCTGTG AAGCAGTACA     120

TTTCCAAAAT GATAGAGGAC AGCGGGCCTG TATGAAAGT ACTTCTCATG GATAAAGAGA     180

CGACTGGCAT AGTGAGTATG GTATACACAC AATCGGAGAT TCTACAGAAG GAAGTGTACC     240

TCTTTGAACG CATCGATTCT CAAAATCGAG AGATCATGAA ACACCTGAAG GCAATTTGTT     300

TTCTTCGACC TACAAAGGAG AATGTGGATT ATATTATTCA GGAGCTCCGA AGACCCAAAT     360

ACACTATATA TTTCATTTAT TTCAGTAATG TGATCAGCAA GAGTGACGTG AAGTCATTGG     420

CTGAAGCTGA TGAACAGGAA GTTGTGGCTG AGGTTCAGGA ATTTTATGGT GATTACATTG     480

CTGTGAACCC ACATTTGTTT TCCCTCAATA TTTTGGGTTG CTGCCAGGGT CGAAATTGGG     540

ATCCAGCCCA GCTATCTAGA ACAACTCAAG GGCTTACAGC TCTCCTTTTA TCTCTGAAGA     600

AGTGTCCCAT GATTCGTTAT CAGCTCTCAT CAGAGGCAGC AAAGAGACTT GCAGAGTGCG     660

TTAAGCAAGT GATAACTAAA GAATATGAAC TGTTTGAATT CCGTCGGACA GAGGTTCCTC     720

CATTGCTCCT TATTTTAGAT CGCTGTGATG ATGCCATCAC CCCATTGCTA AACCAGTGGA     780

CATATCAGGC CATGGTCCAC GAACTACTAG GCATAAACAA CAATCGGATT GATCTTTCCA     840

GAGTGCCGGG AATCAGTAAA GACTTAAGAG AAGTGGTCCT ATCTGCTGAA ATGATGAAT     900

TCTATGCTAA TAATATGTAC CTGAACTTTG CTGAGATTGG TAGCAATATA AAGAATCTCA     960

TGGAAGATTT TCAGAAGAAG AAACCAAAAG AACAGCAAAA ACTAGAATCA ATAGCAGACA    1020

TGAAGGCGTT TGTTGAGAAT TATCCACAGT TCAAGAAAAT GTCTGGGACT GTTTCAAAGC    1080

ATGTGACAGT GGTTGGAGAA CTGTCTCGAT TGGTCAGTGA ACGGAATCTG CTGGAGGTTT    1140

CAGAGGTTGA GCAAGAACTG GCCTGTCAAA ATGACCATTC TAGTGCTCTC CAGAATATAA    1200

AAAGGCTTCT GCAGAACCCC AAAGTGACAG AGTTTGATGC TGCCCGCCTG GTGATGCTTT    1260

ATGCTTTACA TTATGAGCGA CACAGCAGCA ATAGCCTGCC AGGACTAATG ATGGACCTCA    1320

GGAATAAAGG TGTTTCTGAG AAGTATCGAA AGCTCGTGTC TGCAGTTGTT GAATATGGTG    1380

GTAAACGAGT CAGAGGAAGT GACCTCTTCA GCCCCAAAGA TGCTGTGGCT ATCACCAAAC    1440

AATTCCTCAA AGGACTGAAG GGAGTAGAAA ATGTATATAC ACAGCATCAA CCTTTCCTAC    1500

ATGAAACCCT GGATCATCTC ATCAAAGGAA GGCTTAAGGA AAACCTATAT CCTTATTTAG    1560

GCCCCAGCAC ACTCAGAGAC AGACCTCAGG ATATCATTGT GTTTGTAATT GGAGGAGCCA    1620
```

```
CCTATGAAGA GGCTCTAACA GTTTATAACC TGAACCGCAC CACTCCTGGA GTGAGGATTG    1680

TCCTGGGAGG CACCACAGTG CACAACACGA AAAGTTTCCT AGAGGAAGTT CTGGCTTCTG    1740

GACTGCACAG CCGAAGCAAG GAGAGCTCTC AAGTCACATC AAGGTCAGCG AGCAGAAGAT    1800

GAAACGGTGG TTGGGGGAAG GGCACAGCTT CCTCTCTTGT CCCCACTACA GGTTTTCCCT    1860

ACTAAACAAA GGTGTTGGAG AGCAGCTTTG GGTTCTGTGC TGGTTGTTAG AACTCATCTC    1920

CAGGTAGCCC ACGGATACGT GGTTGGCACA GACACAAGAC TCCCAGAGTT GTCCTAACAA    1980

TAAGTCTGAG CCCATCTCAA CCCACTTTTC TCCGGTAGTC TTTATGTATC TGTTAGCACA    2040

ATCACTTCAG TTACTGATGA ATTTGTTGG GATCTGACTT GGGGAAAGGG TTATCAGAGC     2100

CTAGAGGGGC TTAAAAGTA ATCATTTGAT GTACATACCA CACTCCTTGG CTTCCTTTCT     2160

CTTCCCTTAA CCCTTTCTGC TTTTCATTAA CCACATTCCT GCACAACTCA TTTCTGAAAA    2220

CCTACCATGT TTCTTTACAG AGCCATCCAA AAATTTTTTG TCCCTACATA GCAATTTTCT    2280

GTGGCACTGA GAAACCATGT ATGACCACAA TAAAAATCCA TTTTGTGAAA GGAAAAAAAA    2340

AA                                                                    2342

(2) INFORMATION FOR SEQ ID NO: 3:

(i) SEQUENCE CHARACTERISTICS:
        (A) LENGTH: 194 amino acids
        (B) TYPE: amino acid
        (C) STRANDEDNESS: single
        (D) TOPOLOGY: linear (vii) IMMEDIATE SOURCE:
        (A) LIBRARY: 2056691
        (B) CLONE: BEP1NOT01

(xi) SEQUENCE DESCRIPTION: SEQ ID NO: 3:

Met Lys Ile Trp Thr Ser Glu His Val Phe Asp His Pro Trp Glu Thr
1               5                   10                  15

Val Thr Thr Ala Ala Met Gln Lys Tyr Pro Asn Pro Met Asn Pro Ser
            20                  25                  30

Val Val Gly Val Asp Val Leu Asp Arg His Ile Asp Pro Ser Gly Lys
        35                  40                  45

Leu His Ser His Arg Leu Leu Ser Thr Glu Trp Gly Leu Pro Ser Ile
    50                  55                  60

Val Lys Ser Leu Ile Gly Ala Ala Arg Thr Lys Thr Tyr Val Gln Glu
65                  70                  75                  80

His Ser Val Val Asp Pro Val Glu Lys Thr Met Glu Leu Lys Ser Thr
            85                  90                  95

Asn Ile Ser Phe Thr Asn Met Val Ser Val Asp Glu Arg Leu Ile Tyr
            100                 105                 110

Lys Pro His Pro Gln Asp Pro Glu Lys Thr Val Leu Thr Gln Glu Ala
        115                 120                 125

Ile Ile Thr Val Lys Gly Val Ser Leu Ser Ser Tyr Leu Glu Gly Leu
        130                 135                 140

Met Ala Ser Thr Ile Ser Ser Asn Ala Ser Lys Gly Arg Glu Ala Met
145                 150                 155                 160

Glu Trp Val Ile His Lys Leu Asn Ala Glu Ile Glu Glu Leu Thr Ala
            165                 170                 175

Ser Ala Arg Gly Thr Ile Arg Thr Pro Met Ala Ala Ala Phe Ala
        180                 185                 190

Glu Lys
```

-continued (2) INFORMATION FOR SEQ ID NO: 4:

(i) SEQUENCE CHARACTERISTICS:
        (A) LENGTH: 836 base pairs
        (B) TYPE: nucleic acid
        (C) STRANDEDNESS: single
        (D) TOPOLOGY: linear (vii) IMMEDIATE SOURCE:
        (A) LIBRARY: 2056691
        (B) CLONE: BEP1NOT01

(xi) SEQUENCE DESCRIPTION: SEQ ID NO: 4:

```
GAGCGGGGCA GGGGCAGGTG TAGCCTCTGT GCCTCGTTGT CCCCTGGCGC TACCCGGACA      60
TCTCTCAGGG TGCCGGCACC ATGAAGATCT GGACTTCGGA GCACGTCTTT GACCACCCGT     120
GGGAAACTGT TACAACAGCT GCAATGCAGA AATACCCAAA CCCTATGAAC CAAGTGTGG      180
TTGGAGTTGA TGTGTTGGAC AGACATATAG ATCCCTCTGG AAAGTTGCAC AGCCACAGAC     240
TTCTCAGCAC AGAGTGGGGA CTGCCTTCCA TTGTGAAGTC TCTTATTGGT GCAGCAAGAA     300
CGAAAACATA TGTGCAAGAA CATTCTGTAG TTGATCCTGT AGAGAAAACA ATGGAACTTA     360
AATCTACTAA TATTTCATTT ACAAACATGG TTTCAGTAGA TGAGACTT ATATACAAAC       420
CACATCCTCA GGATCCAGAA AAACTGTTTT TGACACAAGA AGCCATAATT ACCGTGAAAG     480
GAGTTAGCCT CAGCAGTTAC CTTGAAGGAC TGATGGCAAG TACGATATCC TCAAATGCTA     540
GTAAAGGCCG AGAAGCAATG GAATGGGTAA TACATAAATT AAATGCTGAG ATTGAAGAAC     600
TGACAGCCTC AGCAAGAGGA ACCATAAGGA CTCCAATGGC AGCAGCAGCG TTTGCAGAGA     660
AGTGATCGTG ACAGTTGGTA GACAACATCG GGTACTCCAG GTCTCTCCAA ACTGACTATA    720
TATTTATTTG TTATTTTAAA AATACAACTA TATTTTGGGT AGTTTTTTTT TTTTTTTTT     780
TTGATAAGTT GGTGTAAGGC TATGTGACTG ATCAAAACAG ATGCAGGGCC TCTAAA        836
```

(2) INFORMATION FOR SEQ ID NO: 5:

(i) SEQUENCE CHARACTERISTICS:
        (A) LENGTH: 177 amino acids
        (B) TYPE: amino acid
        (C) STRANDEDNESS: single
        (D) TOPOLOGY: linear (vii) IMMEDIATE SOURCE:
        (A) LIBRARY: HEAONOT03
        (B) CLONE: 3086794

(xi) SEQUENCE DESCRIPTION: SEQ ID NO: 5:

```
Met Glu Ala Leu Ile Leu Glu Pro Ser Leu Tyr Thr Val Lys Ala Ile
 1               5                  10                  15

Leu Ile Leu Asp Asn Asp Gly Asp Arg Leu Phe Ala Lys Tyr Tyr Asp
            20                  25                  30

Asp Thr Tyr Pro Ser Val Lys Glu Gln Lys Ala Phe Glu Lys Asn Ile
        35                  40                  45

Phe Asn Lys Thr His Arg Thr Asp Ser Glu Ile Ala Leu Leu Glu Gly
    50                  55                  60

Leu Thr Val Val Tyr Lys Ser Ser Ile Asp Leu Tyr Phe Tyr Val Ile
65                  70                  75                  80

Gly Ser Ser Tyr Glu Asn Glu Leu Met Leu Met Ala Val Leu Asn Cys
                85                  90                  95

Leu Phe Asp Ser Leu Ser Gln Met Leu Arg Lys Asn Val Glu Lys Arg
            100                 105                 110

Ala Leu Leu Glu Asn Met Glu Gly Leu Phe Leu Ala Val Asp Glu Ile
        115                 120                 125
```

```
Val Asp Gly Gly Val Ile Leu Glu Ser Asp Pro Gln Gln Val Val His
    130                 135                 140

Arg Val Ala Leu Arg Gly Glu Asp Val Pro Leu Thr Glu Gln Thr Val
145                 150                 155                 160

Ser Gln Val Leu Gln Ser Ala Lys Glu Gln Ile Lys Trp Ser Leu Leu
                165                 170                 175

Arg (2) INFORMATION FOR SEQ ID NO: 6:

(i) SEQUENCE CHARACTERISTICS:
        (A) LENGTH: 1932 base pairs
        (B) TYPE: nucleic acid
        (C) STRANDEDNESS: single
        (D) TOPOLOGY: linear (vii) IMMEDIATE SOURCE:
        (A) LIBRARY: 3086794
        (B) CLONE: HEAONOT03

(xi) SEQUENCE DESCRIPTION: SEQ ID NO: 6:

GGCCAATCAG CGGCGGCGTT TCTTTTGCGG CTCCACGTCG GCACCAGCTG CGGGGCAAGA      60

TGGAGGCGCT GATTTTGGAA CCTTCCCTGT ATACTGTCAA AGCCATCCTG ATTCTGGACA     120

ATGATGGAGA TCGACTTTTT GCCAAGTACT ATGACGACAC CTACCCCAGT GTCAAGGAGC     180

AAAAGGCCTT TGAGAAGAAC ATTTTCAACA AGACCCATCG GACTGACAGT GAAATTGCCC     240

TCTTGGAAGG CCTGACAGTG GTATACAAAA GCAGTATAGA TCTCTATTTC TATGTGATTG     300

GCAGCTCCTA TGAAAATGAG CTGATGCTTA TGGCTGTTCT GAACTGTCTC TTCGACTCAT     360

TGAGCCAGAT GCTGAGGAAA AATGTAGAAA AGCGAGCACT GCTGGAGAAC ATGGAGGGGC     420

TGTTCTTGGC TGTGGATGAA ATTGTAGATG GAGGGGTGAT CCTAGAGAGT GATCCCCAGC     480

AGGTGGTACA CCGGGTGGCA TTAAGGGGTG AAGATGTCCC CCTTACGGAG CAGACCGTGT     540

CTCAGGTGCT GCAGTCAGCC AAAGAACAGA TCAAGTGGTC ACTCCTTCGG TGAAGACCTC     600

ACTGTTCCTG GCTCTTCATC CTCTTCAAAA AATTTGCATG TCTGCTGTGA ATTTTCATCT     660

AGTTCCCCAA TCGATGCTCT CAGGGTCATC TCGGGGATCA CAGGGATCCT TAAATCTCCA     720

TTCTGTTTGT GGTTGCCCCC TCAACCTCCC CTACACCCTT CCTATTCTTT TTCATTCTTC     780

TTGCAGTTCT GGGAGTAAAG CTCCCAGCAT ATTTAGATAA TAGGGCAGGG GAAGCACCCT     840

CTTTCTTTCT AGACTGGATT ATGCTCACAT GCTCCCTTGC CCTGACATTT TTGTAAATTC     900

TGTGCCCTTT GCTGTAGCTA CACTTCAGAT TAAAGTAGGA GAAAGAATGT GCTGAGTGTT     960

TTCCTCCCTT TGCCTCTACC TGGCCCTCAT CCCAACAGCC CAGCAAGGGG AGAGAGAAAG    1020

AGAATTCTTT TCTATAGAAC GAGTGGGGGC GGGGATGGGT AGGGATTTAT CCAATCTAAG    1080

CCCTAACCCC ACTTAGTGAC CTCAGTGTTT TCTTCCATTC CTTCTTACTG CCCTGTCCTC    1140

TGCCTTGGAA GAGGCTTTGG GAATAGTTCA TAGGGAAGGG ACAACATGGA AGAAACAGCG    1200

ATTTAAATTG TATTGAACAG GGCATATAAA ATGCATTCTG TACCCTGATC TGGCATATAG    1260

CTTCAAAACT GCAGTGGCGA GTGTCCATCT CTTAGTTAGC TACCTTAACT GTCCACCCTT    1320

ACTACCTGTG GGATCGTTGC CTGGTTTGTC TTCTCTGTGT CCTGGAGCAA AGCCAGTTCC    1380

TAAAACTAAA ACTCCATTCT AGTCTTGGGA AGAAAAGTTT CTACTCAGAA CTGGGGAAGG    1440

AGTGGAACTT ATGACTTGGG CCTCTAGGCT GTCTCTGTCC CCTCAGCTCC CCGACATGCA    1500

TTTACTCTCT GCCGTGGGTC TGCAGTCGCT GCAACCTACC CTCTCTCTGC CTCAGCCTTA    1560

CACCCAAGCA GTAGGTCTGT GCTCTCCCTG TCTCTAGGTC GCTGAGAGAG GTGCTTTTCT    1620
```

```
TCATAAAACC TTTGGGGTTT GGATTTCCCC AGGAAGATGG AGAATGGAAT ACTCACTCTT    1680

GGGTCTAATC TTTCCCCTTG ACCCAGAACT TCCTCCCCAC AAAAATGCCT TTAAAAACCT    1740

TCCTGAGACT TAAGCATTCT GCCCCACTTA CTAACTGCCA GTTCTCCAGC ACTGAGGTGG    1800

GGCAGATAAC TGGGCATATT TAAGGGGGCA TCTTTGTGTA AAGATGCAT GGAGTCAGGA     1860

GAAAACCACC TTCATAAACT GCTCTGTGCA AAGAGGAATA AAACATTTTT TCCAAAAAAA    1920

AAAAAAAAAA AA                                                        1932
```

(2) INFORMATION FOR SEQ ID NO: 7:

(i) SEQUENCE CHARACTERISTICS:
        (A) LENGTH: 570 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: GI7703494

(xi) SEQUENCE DESCRIPTION: SEQ ID NO: 7:

```
Met Asn Val Val Phe Ala Val Lys Gln Tyr Ile Ser Lys Met Ile Glu
 1               5                  10                  15

Asp Ser Gly Pro Gly Met Lys Val Leu Leu Met Asp Lys Glu Thr Thr
            20                  25                  30

Gly Ile Val Ser Met Val Tyr Thr Gln Ser Glu Ile Leu Gln Lys Glu
        35                  40                  45

Val Tyr Leu Phe Glu Arg Ile Asp Ser Gln Asn Arg Glu Ile Met Lys
    50                  55                  60

His Leu Lys Ala Ile Cys Phe Leu Arg Pro Thr Lys Glu Asn Val Glu
65                  70                  75                  80

Tyr Leu Ile Gln Glu Leu Arg Arg Pro Lys Tyr Ser Ile Tyr Phe Ile
                85                  90                  95

Tyr Phe Ser Asn Val Ile Ser Lys Ser Asp Val Lys Ser Leu Ala Glu
            100                 105                 110

Ala Asp Glu Gln Glu Val Val Ala Glu Val Gln Glu Phe Tyr Gly Asp
        115                 120                 125

Tyr Ile Ala Val Asn Pro His Leu Phe Ser Leu Asn Ile Leu Gly Cys
    130                 135                 140

Cys Gln Gly Arg Asn Trp Asp Pro Ala Gln Leu Ser Arg Thr Thr Gln
145                 150                 155                 160

Gly Leu Thr Ala Leu Leu Leu Ser Leu Lys Lys Cys Pro Met Ile Arg
                165                 170                 175

Tyr Gln Leu Ser Ser Glu Ala Ala Lys Arg Leu Gly Glu Cys Val Lys
            180                 185                 190

Gln Val Ile Ser Lys Glu Tyr Glu Leu Phe Glu Phe Arg Arg Thr Glu
        195                 200                 205

Val Pro Pro Leu Leu Leu Ile Leu Asp Arg Cys Asp Asp Ala Ile Thr
    210                 215                 220

Pro Leu Leu Asn Gln Trp Thr Tyr Gln Ala Met Val His Glu Leu Leu
225                 230                 235                 240

Gly Ile Asn Asn Asn Arg Ile Asp Leu Ser Arg Val Pro Gly Ile Ser
                245                 250                 255

Lys Asp Leu Arg Glu Val Val Leu Ser Ala Glu Asn Asp Glu Phe Tyr
            260                 265                 270

Ala Asn Asn Met Tyr Leu Asn Phe Ala Glu Ile Gly Ser Asn Ile Lys
```

-continued

```
                        275                 280                 285
Asn Leu Met Glu Asp Phe Gln Lys Lys Arg Pro Lys Glu Gln Gln Lys
290                 295                 300
Leu Glu Ser Ile Ala Asp Met Lys Ala Phe Val Glu Asn Tyr Pro Gln
305                 310                 315                 320
Phe Lys Lys Met Ser Gly Thr Val Ser Lys His Val Thr Val Val Gly
                325                 330                 335
Glu Leu Ser Arg Leu Val Ser Glu Arg Asn Leu Leu Glu Val Ser Glu
            340                 345                 350
Val Glu Gln Glu Leu Ala Cys Gln Asn Asp His Ser Ser Ala Leu Gln
        355                 360                 365
Asn Val Lys Arg Leu Leu Gln Asn Pro Lys Val Thr Glu Phe Asp Ala
    370                 375                 380
Val Arg Leu Val Met Leu Tyr Ala Leu His Tyr Glu Arg His Ser Ser
385                 390                 395                 400
Asn Ser Leu Pro Gly Leu Ile Val Asp Leu Arg Ser Lys Gly Val Ala
                405                 410                 415
Glu Lys Tyr Arg Lys Leu Val Ser Ala Val Val Glu Tyr Gly Gly Lys
            420                 425                 430
Arg Val Arg Gly Ser Asp Leu Phe Ser Pro Lys Asp Ala Val Ala Ile
        435                 440                 445
Thr Lys Gln Phe Leu Lys Gly Leu Lys Gly Val Glu Asn Val Tyr Thr
    450                 455                 460
Gln His Gln Pro Phe Leu His Glu Thr Leu Asp His Leu Ile Lys Gly
465                 470                 475                 480
Arg Leu Lys Glu Asn Leu Tyr Pro Tyr Leu Gly Pro Ser Thr Leu Arg
                485                 490                 495
Asp Arg Pro Gln Asp Ile Ile Val Phe Ile Ile Gly Gly Ala Thr Tyr
            500                 505                 510
Glu Glu Ala Leu Thr Val Tyr Asn Leu Asn Arg Thr Thr Pro Gly Val
        515                 520                 525
Arg Ile Val Leu Gly Gly Thr Thr Ile His Asn Thr Lys Ser Phe Leu
    530                 535                 540
Glu Glu Val Leu Ala Ser Gly Leu His Ser Arg Ser Arg Glu Ser Ser
545                 550                 555                 560
Gln Ala Thr Ser Arg Ser Ala Asn Arg Arg
                565                 570

(2) INFORMATION FOR SEQ ID NO: 8:

(i) SEQUENCE CHARACTERISTICS:
        (A) LENGTH: 215 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: GI969170

(xi) SEQUENCE DESCRIPTION: SEQ ID NO: 8:

Met Gly Lys Tyr Cys Ala Ser Leu Gly Val Leu Lys Gly Pro Trp Asp
1               5                   10                  15
Gln Val Phe Ala Ala Phe Trp Gln Arg Tyr Pro Asn Pro Tyr Ser Lys
                20                  25                  30
His Val Leu Thr Glu Asp Ile Val His Arg Glu Val Thr Ala Asp His
            35                  40                  45
```

```
Lys Leu Leu Ser Arg Arg Leu Leu Thr Lys Thr Asn Arg Met Pro Arg
    50                  55                  60

Trp Ala Glu Arg Phe Phe Pro Ala Asn Val Ala His Asn Val Tyr Ile
 65                  70                  75                  80

Val Glu Asp Ser Ile Val Asp Pro Lys Asn Arg Thr Met Thr Thr Phe
                85                  90                  95

Thr Trp Asn Ile Asn His Ala Arg Leu Met Ala Val Glu Glu Arg Cys
               100                 105                 110

Val Tyr Arg Val Asn Pro Glu Asn Ser Ser Trp Thr Glu Val Lys Arg
           115                 120                 125

Glu Ala Trp Val Ser Ser Leu Phe Gly Val Ser Arg Ala Val Gln
   130                 135                 140

Glu Phe Gly Leu Ala Arg Phe Lys Ser Asn Val Thr Lys Ser Thr Lys
145                 150                 155                 160

Gly Phe Glu Tyr Val Leu Ala Arg Met Gln Gly Glu Ala Pro Ser Lys
                165                 170                 175

Thr Leu Val Glu Thr Ala Lys Glu Ala Thr Glu Lys Ala Lys Glu Thr
               180                 185                 190

Ala Leu Ala Ala Thr Glu Lys Ala Lys Asp Leu Ala Ser Lys Ala Ala
           195                 200                 205

Thr Lys Lys Lys Gln Phe Val
           210                 215

(2) INFORMATION FOR SEQ ID NO: 9:

(i) SEQUENCE CHARACTERISTICS:
        (A) LENGTH: 177 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: GI441486

(xi) SEQUENCE DESCRIPTION: SEQ ID NO: 9:

Met Glu Ala Leu Ile Leu Gln Pro Ser Leu Tyr Thr Val Lys Ala Ile
 1                   5                  10                  15

Leu Ile Leu Asp Asn Asp Gly Asp Arg Leu Phe Ala Lys Tyr Tyr Asp
                20                  25                  30

Asp Thr Tyr Pro Ser Val Lys Glu Gln Lys Ala Phe Glu Lys Asn Ile
                35                  40                  45

Phe Asn Lys Thr His Arg Thr Asp Ser Glu Ile Ala Leu Leu Glu Gly
    50                  55                  60

Leu Thr Val Val Tyr Lys Ser Ser Ile Asp Leu Tyr Phe Tyr Val Ile
 65                  70                  75                  80

Gly Ser Ser Tyr Glu Asn Glu Leu Met Leu Met Thr Val Leu Asn Cys
                85                  90                  95

Leu Phe Asp Ser Leu Ser Gln Met Leu Arg Lys Asn Val Glu Lys Arg
               100                 105                 110

Ala Leu Leu Glu Asn Met Glu Gly Leu Phe Leu Ala Val Asp Glu Ile
           115                 120                 125

Val Asp Gly Gly Val Ile Leu Glu Ser Asp Pro Gln Gln Val Val His
           130                 135                 140

Arg Val Ala Leu Arg Gly Glu Asp Val Pro Leu Thr Glu Gln Thr Val
145                 150                 155                 160
```

```
Ser Gln Val Leu Gln Ser Ala Lys Glu Gln Ile Lys Trp Ser Leu Leu
                165                 170                 175
Arg
```